US012070432B2

(12) United States Patent
Tourchak et al.

(10) Patent No.: US 12,070,432 B2
(45) Date of Patent: Aug. 27, 2024

(54) URINE COLLECTION SYSTEM INCLUDING A FLOW METER AND RELATED METHODS

(71) Applicant: PureWick Corporation, El Cajon, CA (US)

(72) Inventors: Michelle Tourchak, Alpharetta, GA (US); Kristin Watson, Social Circle, GA (US); Jill W. Jones, Atlanta, GA (US); Hollie Trullenque, Atlanta, GA (US); Gina Whitlock, Barrington Hills, IL (US); Mark Weissmann, Grapevine, TX (US); Adam Voigt, Chapin, SC (US); Cecille Canary, Atlanta, GA (US)

(73) Assignee: PureWick Corporation, Covington, GA (US)

( * ) Notice: Subject to any disclaimer, the term of this patent is extended or adjusted under 35 U.S.C. 154(b) by 351 days.

(21) Appl. No.: 17/453,560

(22) Filed: Nov. 4, 2021

(65) Prior Publication Data

US 2022/0142843 A1   May 12, 2022

Related U.S. Application Data

(60) Provisional application No. 63/112,417, filed on Nov. 11, 2020.

(51) Int. Cl.
*A61G 9/00* (2006.01)
*A61M 1/00* (2006.01)
*G16H 10/60* (2018.01)

(52) U.S. Cl.
CPC .............. *A61G 9/003* (2013.01); *A61M 1/64* (2021.05); *A61M 1/71* (2021.05); *G16H 10/60* (2018.01);

(Continued)

(58) Field of Classification Search
CPC ........... A61G 9/003; A61M 1/64; A61M 1/71; A61M 2202/0496; A61M 2205/3331;
(Continued)

(56) References Cited

U.S. PATENT DOCUMENTS 1,032,841 A   7/1912   Koenig
1,178,644 A   4/1916   Johnson
(Continued)

FOREIGN PATENT DOCUMENTS

AU   2018216821 A1   8/2019
CA   2165286 C   9/1999
(Continued)

OTHER PUBLICATIONS

US 9,908,683 B2, 03/2018, Sandhausen et al. (withdrawn)
(Continued)

*Primary Examiner* — Lori L Baker
(74) *Attorney, Agent, or Firm* — Dorsey & Whitney LLP

(57) ABSTRACT

A urine collection system includes a urine collection device configured to collect urine discharged from a user and a urine collection container in fluid communication with the urine collection device and sized and dimensioned to receive the urine discharged from the user. The urine collection system also includes a flow meter having a communication interface and positioned between the urine collection container and the urine collection device. The flow meter is configured to detect a flow property of the urine at least related to a volume of the urine entering the urine collection container and the communication interface is configured to wirelessly communicate to a computing device at least one of the detected flow property or the volume of the urine including the volume of the urine discharged from the user entering the urine collection container.

23 Claims, 6 Drawing Sheets

(52) U.S. Cl.
CPC ............. *A61M 2202/0496* (2013.01); *A61M 2205/3331* (2013.01); *A61M 2205/3379* (2013.01); *A61M 2205/3553* (2013.01); *A61M 2205/583* (2013.01)

(58) Field of Classification Search
CPC .. A61M 2205/3379; A61M 2205/3553; A61M 2205/583; A61M 1/80; A61M 2205/3334; A61M 2205/3569; A61M 2205/50; A61M 2205/8206; A61M 1/60; A61M 1/73; G16H 10/60; G16H 40/63; A61F 5/4408; A61F 5/451
USPC ............................................ 4/454–455, 450
See application file for complete search history.

(56) References Cited

U.S. PATENT DOCUMENTS

| | | |
|---|---|---|
| 1,742,080 A | 12/1929 | Jones |
| 1,979,899 A | 11/1934 | Obrien et al. |
| 2,262,772 A | 11/1941 | Peder |
| 2,326,881 A | 8/1943 | Packer |
| 2,379,346 A | 6/1945 | Farrell |
| 2,613,670 A | 10/1952 | Edward |
| 2,616,426 A | 11/1952 | Adele |
| 2,644,234 A | 7/1953 | Earl |
| 2,648,335 A | 8/1953 | Chambers |
| 2,859,786 A | 11/1958 | Tupper |
| 2,944,551 A | 7/1960 | Carl |
| 2,968,046 A | 1/1961 | Duke |
| 2,971,512 A | 2/1961 | Reinhardt |
| 3,032,038 A | 5/1962 | Swinn |
| 3,077,883 A | 2/1963 | Hill |
| 3,087,938 A | 4/1963 | Hans et al. |
| 3,169,528 A | 2/1965 | Knox et al. |
| 3,194,238 A | 7/1965 | Breece |
| 3,198,994 A | 8/1965 | Hildebrandt et al. |
| 3,221,742 A | 12/1965 | Egon |
| 3,312,221 A | 4/1967 | Overment |
| 3,312,981 A | 4/1967 | McGuire et al. |
| 3,349,768 A | 10/1967 | Keane |
| 3,362,590 A | 1/1968 | Gene |
| 3,366,116 A | 1/1968 | Huck |
| 3,398,848 A | 8/1968 | Donovan |
| 3,400,717 A | 9/1968 | Bruce et al. |
| 3,406,688 A | 10/1968 | Bruce |
| 3,424,163 A | 1/1969 | Gravdahl |
| 3,425,471 A | 2/1969 | Yates |
| 3,511,241 A | 5/1970 | Lee |
| 3,512,185 A | 5/1970 | Ellis |
| 3,520,300 A | 7/1970 | Flower |
| 3,528,423 A | 9/1970 | Lee |
| 3,613,123 A | 10/1971 | Langstrom |
| 3,648,700 A | 3/1972 | Warner |
| 3,651,810 A | 3/1972 | Ormerod |
| 3,661,155 A | 5/1972 | Lindan |
| 3,699,815 A | 10/1972 | Holbrook |
| 3,726,277 A | 4/1973 | Hirschman |
| 3,742,952 A | 7/1973 | Magers et al. |
| 3,757,355 A | 9/1973 | Allen et al. |
| 3,788,324 A | 1/1974 | Lim |
| 3,843,016 A | 10/1974 | Bornhorst et al. |
| 3,863,638 A | 2/1975 | Rogers et al. |
| 3,863,798 A | 2/1975 | Kurihara et al. |
| 3,864,759 A | 2/1975 | Horiuchi |
| 3,881,486 A | 5/1975 | Fenton |
| 3,915,189 A | 10/1975 | Holbrook et al. |
| 3,998,228 A | 12/1976 | Poidomani |
| 3,999,550 A | 12/1976 | Martin |
| 4,015,604 A | 4/1977 | Csillag |
| 4,020,843 A | 5/1977 | Kanall |
| 4,022,213 A | 5/1977 | Stein |
| 4,027,776 A | 6/1977 | Douglas |
| 4,116,197 A | 9/1978 | Bermingham |
| 4,180,178 A | 12/1979 | Turner |
| 4,187,953 A | 2/1980 | Turner |
| 4,194,508 A | 3/1980 | Anderson |
| 4,200,102 A | 4/1980 | Duhamel et al. |
| 4,202,058 A | 5/1980 | Anderson |
| 4,233,025 A | 11/1980 | Larson et al. |
| 4,233,978 A | 11/1980 | Hickey |
| 4,246,901 A | 1/1981 | Frosch et al. |
| 4,257,418 A | 3/1981 | Hessner |
| 4,270,539 A | 6/1981 | Frosch et al. |
| 4,281,655 A | 8/1981 | Terauchi |
| 4,292,916 A | 10/1981 | Bradley et al. |
| 4,352,356 A | 10/1982 | Tong |
| 4,360,933 A | 11/1982 | Kimura et al. |
| 4,365,363 A | 12/1982 | Windauer |
| 4,387,726 A | 6/1983 | Denard |
| 4,425,130 A | 1/1984 | Desmarais |
| 4,446,986 A | 5/1984 | Bowen et al. |
| 4,453,938 A | 6/1984 | Brendling |
| 4,457,314 A | 7/1984 | Knowles |
| 4,476,879 A | 10/1984 | Jackson |
| 4,526,688 A | 7/1985 | Schmidt et al. |
| 4,528,703 A | 7/1985 | Kraus |
| D280,438 S | 9/1985 | Wendt |
| 4,551,141 A | 11/1985 | Mcneil |
| 4,553,968 A | 11/1985 | Komis |
| 4,581,026 A | 4/1986 | Schneider |
| 4,610,675 A | 9/1986 | Triunfol |
| 4,620,333 A | 11/1986 | Ritter |
| 4,626,250 A | 12/1986 | Schneider |
| 4,627,846 A | 12/1986 | Ternstroem |
| 4,631,061 A | 12/1986 | Martin |
| 4,650,477 A | 3/1987 | Johnson |
| 4,656,675 A | 4/1987 | Fajnsztajn |
| 4,681,570 A | 7/1987 | Dalton |
| 4,692,160 A | 9/1987 | Nussbaumer |
| 4,707,864 A | 11/1987 | Ikematsu et al. |
| 4,713,065 A | 12/1987 | Koot |
| 4,713,066 A | 12/1987 | Komis |
| 4,743,236 A * | 5/1988 | Manschot ............. A61F 5/4405 600/580 |
| 4,747,166 A | 5/1988 | Kuntz |
| 4,752,944 A | 6/1988 | Conrads et al. |
| 4,769,215 A | 9/1988 | Ehrenkranz |
| 4,772,280 A | 9/1988 | Rooyakkers |
| 4,790,830 A | 12/1988 | Hamacher |
| 4,790,835 A | 12/1988 | Elias |
| 4,791,686 A | 12/1988 | Taniguchi et al. |
| 4,795,449 A | 1/1989 | Schneider et al. |
| 4,798,603 A | 1/1989 | Meyer et al. |
| 4,799,928 A | 1/1989 | Crowley |
| 4,804,377 A | 2/1989 | Hanifl et al. |
| 4,812,053 A | 3/1989 | Bhattacharjee |
| 4,820,297 A | 4/1989 | Kaufman et al. |
| 4,846,818 A | 7/1989 | Keldahl et al. |
| 4,846,909 A | 7/1989 | Klug et al. |
| 4,865,595 A | 9/1989 | Heyden |
| 4,880,417 A | 11/1989 | Yabrov et al. |
| 4,882,794 A | 11/1989 | Stewart |
| 4,883,465 A | 11/1989 | Brennan |
| 4,886,498 A | 12/1989 | Newton |
| 4,886,508 A | 12/1989 | Washington |
| 4,886,509 A | 12/1989 | Mattsson |
| 4,889,532 A | 12/1989 | Metz et al. |
| 4,889,533 A | 12/1989 | Beecher |
| 4,903,254 A | 2/1990 | Haas |
| 4,905,692 A | 3/1990 | More |
| 4,936,838 A | 6/1990 | Cross et al. |
| 4,955,922 A | 9/1990 | Terauchi |
| 4,957,487 A | 9/1990 | Gerow |
| 4,965,460 A | 10/1990 | Tanaka et al. |
| 4,987,849 A | 1/1991 | Sherman |
| 5,002,541 A | 3/1991 | Conkling et al. |
| 5,004,463 A | 4/1991 | Nigay |
| 5,031,248 A | 7/1991 | Kemper |
| 5,045,077 A | 9/1991 | Blake |
| 5,045,283 A | 9/1991 | Patel |
| 5,049,144 A | 9/1991 | Payton |
| 5,053,339 A | 10/1991 | Patel |
| 5,058,088 A | 10/1991 | Haas et al. |

(56) References Cited

U.S. PATENT DOCUMENTS

| | | |
|---|---|---|
| 5,071,347 A | 12/1991 | McGuire |
| 5,078,707 A | 1/1992 | Peter |
| 5,084,037 A | 1/1992 | Barnett |
| 5,100,396 A | 3/1992 | Zamierowski |
| 5,112,324 A | 5/1992 | Wallace |
| 5,147,301 A | 9/1992 | Ruvio |
| 5,176,667 A | 1/1993 | Debring |
| 5,195,997 A | 3/1993 | Carns |
| 5,203,699 A | 4/1993 | McGuire |
| 5,244,458 A | 9/1993 | Takasu |
| 5,246,454 A | 9/1993 | Peterson |
| 5,267,988 A | 12/1993 | Farkas |
| 5,275,307 A | 1/1994 | Freese |
| 5,294,983 A | 3/1994 | Ersoz et al. |
| 5,295,983 A | 3/1994 | Kubo |
| 5,300,052 A | 4/1994 | Kubo |
| 5,312,383 A | 5/1994 | Kubalak |
| 5,318,550 A | 6/1994 | Cermak et al. |
| 5,340,840 A | 8/1994 | Park et al. |
| 5,382,244 A | 1/1995 | Telang |
| 5,409,014 A * | 4/1995 | Napoli .................... A61B 5/20 600/575 |
| 5,423,784 A | 6/1995 | Metz |
| 5,456,246 A | 10/1995 | Schmieding et al. |
| 5,466,229 A | 11/1995 | Elson et al. |
| 5,478,334 A | 12/1995 | Bernstein |
| 5,499,977 A | 3/1996 | Marx |
| 5,543,042 A | 8/1996 | Filan et al. |
| D373,928 S | 9/1996 | Green |
| 5,605,161 A | 2/1997 | Cross |
| 5,618,277 A | 4/1997 | Goulter |
| 5,628,735 A | 5/1997 | Skow |
| 5,636,643 A | 6/1997 | Argenta et al. |
| 5,637,104 A | 6/1997 | Ball et al. |
| 5,674,212 A | 10/1997 | Osborn et al. |
| 5,678,564 A | 10/1997 | Lawrence et al. |
| 5,678,654 A | 10/1997 | Uzawa |
| 5,687,429 A | 11/1997 | Rahlff |
| 5,695,485 A | 12/1997 | Duperret et al. |
| 5,752,944 A | 5/1998 | Dann et al. |
| 5,772,644 A | 6/1998 | Bark et al. |
| 5,792,132 A | 8/1998 | Garcia |
| 5,827,243 A | 10/1998 | Palestrant |
| 5,827,247 A | 10/1998 | Kay |
| 5,827,250 A | 10/1998 | Fujioka et al. |
| 5,827,257 A | 10/1998 | Fujioka et al. |
| D401,699 S | 11/1998 | Herchenbach et al. |
| 5,865,378 A | 2/1999 | Hollinshead et al. |
| 5,887,291 A | 3/1999 | Bellizzi |
| 5,894,608 A | 4/1999 | Birbara |
| D409,303 S | 5/1999 | Oepping |
| 5,911,222 A | 6/1999 | Lawrence et al. |
| 5,957,904 A | 9/1999 | Holland |
| 5,968,026 A | 10/1999 | Osborn et al. |
| 5,972,505 A | 10/1999 | Phillips et al. |
| 6,039,060 A | 3/2000 | Rower |
| 6,050,983 A | 4/2000 | Moore et al. |
| 6,059,762 A | 5/2000 | Boyer et al. |
| 6,063,064 A | 5/2000 | Tuckey et al. |
| 6,098,625 A | 8/2000 | Winkler |
| 6,105,174 A | 8/2000 | Karlsten et al. |
| 6,113,582 A | 9/2000 | Dwork |
| 6,117,163 A | 9/2000 | Bierman |
| 6,123,398 A | 9/2000 | Arai et al. |
| 6,129,718 A | 10/2000 | Wada et al. |
| 6,131,964 A | 10/2000 | Sareshwala |
| 6,152,902 A | 11/2000 | Christian et al. |
| 6,164,569 A | 12/2000 | Hollinshead et al. |
| 6,177,606 B1 | 1/2001 | Etheredge et al. |
| 6,209,142 B1 | 4/2001 | Mattsson et al. |
| 6,248,096 B1 | 6/2001 | Dwork et al. |
| 6,263,887 B1 | 7/2001 | Dunn |
| 6,311,339 B1 | 11/2001 | Kraus |
| 6,336,919 B1 | 1/2002 | Davis et al. |
| 6,338,729 B1 | 1/2002 | Wada et al. |
| 6,352,525 B1 | 3/2002 | Wakabayashi |
| 6,394,988 B1 | 5/2002 | Hashimoto |
| 6,398,742 B1 | 6/2002 | Kim |
| 6,406,463 B1 | 6/2002 | Brown |
| 6,409,712 B1 | 6/2002 | Dutari et al. |
| 6,416,500 B1 | 7/2002 | Wada et al. |
| 6,428,521 B1 | 8/2002 | Droll |
| 6,475,198 B1 | 11/2002 | Lipman et al. |
| 6,479,726 B1 | 11/2002 | Cole et al. |
| 6,491,673 B1 | 12/2002 | Palumbo et al. |
| 6,508,794 B1 | 1/2003 | Palumbo et al. |
| 6,540,729 B1 | 4/2003 | Wada et al. |
| 6,547,771 B2 | 4/2003 | Robertson et al. |
| 6,569,133 B2 | 5/2003 | Cheng et al. |
| D476,518 S | 7/2003 | Doppelt |
| 6,592,560 B2 | 7/2003 | Snyder et al. |
| 6,618,868 B2 | 9/2003 | Minnick |
| 6,620,142 B1 | 9/2003 | Flueckiger |
| 6,629,651 B1 | 10/2003 | Male et al. |
| 6,635,038 B2 | 10/2003 | Scovel |
| 6,652,495 B1 | 11/2003 | Walker |
| 6,685,684 B1 | 2/2004 | Falconer |
| 6,702,793 B1 | 3/2004 | Sweetser et al. |
| 6,706,027 B2 | 3/2004 | Harvie et al. |
| 6,732,384 B2 | 5/2004 | Scott |
| 6,736,977 B1 | 5/2004 | Hall et al. |
| 6,740,066 B2 | 5/2004 | Wolff et al. |
| 6,764,477 B1 | 7/2004 | Chen et al. |
| 6,783,519 B2 | 8/2004 | Samuelsson |
| 6,796,974 B2 | 9/2004 | Palumbo et al. |
| 6,814,547 B2 | 11/2004 | Childers et al. |
| 6,849,065 B2 | 2/2005 | Schmidt et al. |
| 6,857,137 B2 | 2/2005 | Otto |
| 6,885,690 B2 | 4/2005 | Aggerstam et al. |
| 6,888,044 B2 | 5/2005 | Fell et al. |
| 6,893,425 B2 | 5/2005 | Dunn et al. |
| 6,912,737 B2 | 7/2005 | Ernest et al. |
| 6,918,899 B2 | 7/2005 | Harvie |
| 6,979,324 B2 | 12/2005 | Bybordi et al. |
| 7,018,366 B2 | 3/2006 | Easter |
| 7,066,411 B2 | 6/2006 | Male et al. |
| 7,122,023 B1 | 10/2006 | Hinoki |
| 7,125,399 B2 | 10/2006 | Miskie |
| 7,131,964 B2 | 11/2006 | Harvie |
| 7,135,012 B2 | 11/2006 | Harvie |
| 7,141,043 B2 | 11/2006 | Harvie |
| D533,972 S | 12/2006 | La |
| 7,160,273 B2 | 1/2007 | Greter et al. |
| 7,171,699 B2 | 2/2007 | Ernest et al. |
| 7,171,871 B2 | 2/2007 | Kozak |
| 7,179,951 B2 | 2/2007 | Krishnaswamy-Mirle et al. |
| 7,181,781 B1 | 2/2007 | Trabold et al. |
| 7,186,245 B1 | 3/2007 | Cheng et al. |
| 7,192,424 B2 | 3/2007 | Cooper |
| 7,220,250 B2 | 5/2007 | Suzuki et al. |
| D562,975 S | 2/2008 | Otto |
| 7,335,189 B2 | 2/2008 | Harvie |
| 7,358,282 B2 | 4/2008 | Krueger et al. |
| 7,390,320 B2 | 6/2008 | Machida et al. |
| 7,438,706 B2 | 10/2008 | Koizumi et al. |
| 7,488,310 B2 | 2/2009 | Yang |
| 7,491,194 B1 | 2/2009 | Oliwa |
| D591,106 S | 4/2009 | Dominique et al. |
| 7,513,381 B2 | 4/2009 | Heng et al. |
| 7,520,872 B2 | 4/2009 | Biggie et al. |
| D593,801 S | 6/2009 | Wilson et al. |
| 7,540,364 B2 | 6/2009 | Sanderson |
| 7,585,293 B2 | 9/2009 | Vermaak |
| 7,588,560 B1 | 9/2009 | Dunlop |
| 7,665,359 B2 | 2/2010 | Barber |
| 7,682,347 B2 | 3/2010 | Parks et al. |
| 7,687,004 B2 | 3/2010 | Allen |
| 7,695,459 B2 | 4/2010 | Gilbert et al. |
| 7,695,460 B2 | 4/2010 | Wada et al. |
| 7,699,818 B2 | 4/2010 | Gilbert |
| 7,699,831 B2 | 4/2010 | Bengtson et al. |
| 7,722,584 B2 | 5/2010 | Tanaka et al. |
| 7,727,206 B2 | 6/2010 | Gorres |
| 7,740,620 B2 | 6/2010 | Gilbert et al. |

(56) References Cited

U.S. PATENT DOCUMENTS

| | | |
|---|---|---|
| 7,749,205 B2 | 7/2010 | Tazoe et al. |
| 7,755,497 B2 | 7/2010 | Wada et al. |
| 7,766,887 B2 | 8/2010 | Burns et al. |
| D625,407 S | 10/2010 | Koizumi et al. |
| 7,806,879 B2 | 10/2010 | Brooks et al. |
| 7,811,272 B2 | 10/2010 | Lindsay et al. |
| 7,815,067 B2 | 10/2010 | Matsumoto et al. |
| 7,833,169 B2 | 11/2010 | Hannon |
| 7,857,806 B2 | 12/2010 | Karpowicz et al. |
| 7,866,942 B2 | 1/2011 | Harvie |
| 7,871,385 B2 | 1/2011 | Levinson et al. |
| 7,875,010 B2 | 1/2011 | Frazier et al. |
| 7,901,389 B2 | 3/2011 | Mombrinie |
| 7,927,320 B2 | 4/2011 | Goldwasser et al. |
| 7,927,321 B2 | 4/2011 | Marland |
| 7,931,634 B2 | 4/2011 | Swiecicki et al. |
| 7,939,706 B2 | 5/2011 | Okabe et al. |
| 7,946,443 B2 | 5/2011 | Stull et al. |
| 7,947,025 B2 | 5/2011 | Buglino et al. |
| 7,963,419 B2 | 6/2011 | Burney et al. |
| 7,976,519 B2 | 7/2011 | Bubb et al. |
| 7,993,318 B2 | 8/2011 | Olsson et al. |
| 8,015,627 B2 | 9/2011 | Baker et al. |
| 8,028,460 B2 | 10/2011 | Williams |
| 8,047,398 B2 | 11/2011 | Dimartino et al. |
| 8,083,094 B2 | 12/2011 | Caulfield et al. |
| 8,128,608 B2 | 3/2012 | Thevenin |
| 8,181,651 B2 | 5/2012 | Pinel |
| 8,181,819 B2 | 5/2012 | Burney et al. |
| 8,211,063 B2 | 7/2012 | Bierman et al. |
| 8,221,369 B2 | 7/2012 | Parks et al. |
| 8,241,262 B2 | 8/2012 | Mahnensmith |
| 8,277,426 B2 | 10/2012 | Wilcox et al. |
| 8,287,508 B1 | 10/2012 | Sanchez |
| 8,303,554 B2 | 11/2012 | Tsai et al. |
| 8,322,565 B2 | 12/2012 | Caulfield et al. |
| 8,337,477 B2 | 12/2012 | Parks et al. |
| D674,241 S | 1/2013 | Bickert et al. |
| 8,343,122 B2 | 1/2013 | Gorres |
| 8,353,074 B2 | 1/2013 | Krebs |
| 8,353,886 B2 | 1/2013 | Bester et al. |
| D676,241 S | 2/2013 | Merrill |
| 8,388,588 B2 | 3/2013 | Wada et al. |
| D679,807 S | 4/2013 | Burgess et al. |
| 8,425,482 B2 | 4/2013 | Khoubnazar |
| 8,449,510 B2 | 5/2013 | Martini et al. |
| D684,260 S | 6/2013 | Lund et al. |
| 8,470,230 B2 | 6/2013 | Caulfield et al. |
| 8,479,941 B2 | 7/2013 | Matsumoto et al. |
| 8,479,949 B2 | 7/2013 | Henkel |
| 8,500,719 B1 | 8/2013 | Simpson et al. |
| 8,512,301 B2 | 8/2013 | Ma |
| 8,529,530 B2 | 9/2013 | Koch et al. |
| 8,535,284 B2 | 9/2013 | Joder et al. |
| 8,546,639 B2 | 10/2013 | Wada et al. |
| 8,551,075 B2 | 10/2013 | Bengtson |
| 8,568,376 B2 | 10/2013 | Delattre et al. |
| D694,404 S | 11/2013 | Burgess et al. |
| 8,585,683 B2 | 11/2013 | Bengtson et al. |
| 8,652,112 B2 | 2/2014 | Johannison et al. |
| D702,973 S | 4/2014 | Norland et al. |
| 8,703,032 B2 | 4/2014 | Menon et al. |
| D704,330 S | 5/2014 | Cicatelli |
| D704,510 S | 5/2014 | Mason et al. |
| D705,423 S | 5/2014 | Walsh Cutler |
| D705,926 S | 5/2014 | Burgess et al. |
| 8,714,394 B2 | 5/2014 | Wulf |
| 8,715,267 B2 | 5/2014 | Bengtson et al. |
| 8,757,425 B2 | 6/2014 | Copeland |
| 8,777,032 B2 | 7/2014 | Biesecker et al. |
| 8,808,260 B2 | 8/2014 | Koch et al. |
| 8,864,730 B2 | 10/2014 | Conway et al. |
| 8,881,923 B2 | 11/2014 | Higginson |
| 8,882,731 B2 | 11/2014 | Suzuki et al. |
| 8,936,585 B2 | 1/2015 | Carson et al. |
| D729,581 S | 5/2015 | Boroski |
| 9,028,460 B2 | 5/2015 | Medeiros |
| 9,056,698 B2 | 6/2015 | Noer |
| 9,078,792 B2 | 7/2015 | Ruiz |
| 9,173,602 B2 | 11/2015 | Gilbert |
| 9,173,799 B2 | 11/2015 | Tanimoto et al. |
| 9,187,220 B2 | 11/2015 | Biesecker et al. |
| 9,199,772 B2 | 12/2015 | Krippendorf |
| 9,233,020 B2 | 1/2016 | Matsumiya |
| 9,248,058 B2 | 2/2016 | Conway et al. |
| 9,308,118 B1 | 4/2016 | Dupree et al. |
| 9,309,029 B2 | 4/2016 | Incorvia et al. |
| 9,333,281 B2 | 5/2016 | Giezendanner et al. |
| 9,382,047 B2 | 7/2016 | Schmidtner et al. |
| 9,456,937 B2 | 10/2016 | Ellis |
| 9,480,595 B2 | 11/2016 | Baham et al. |
| 9,517,865 B2 | 12/2016 | Albers et al. |
| D777,941 S | 1/2017 | Piramoon |
| 9,533,806 B2 | 1/2017 | Ding et al. |
| 9,550,611 B2 | 1/2017 | Hodge |
| 9,555,930 B2 | 1/2017 | Campbell et al. |
| 9,623,159 B2 | 4/2017 | Locke |
| D789,522 S | 6/2017 | Burgess et al. |
| 9,687,849 B2 | 6/2017 | Bruno et al. |
| 9,694,949 B2 | 7/2017 | Hendricks et al. |
| 9,713,547 B2 | 7/2017 | Lee et al. |
| 9,788,992 B2 | 10/2017 | Harvie |
| D804,907 S | 12/2017 | Sandoval |
| 9,868,564 B2 | 1/2018 | McGirr et al. |
| D814,239 S | 4/2018 | Arora |
| D817,484 S | 5/2018 | Lafond |
| 10,037,640 B2 | 7/2018 | Gordon |
| 10,058,470 B2 | 8/2018 | Phillips |
| 10,098,990 B2 | 10/2018 | Koch et al. |
| D835,264 S | 12/2018 | Mozzicato et al. |
| D835,779 S | 12/2018 | Mozzicato et al. |
| D840,533 S | 2/2019 | Mozzicato et al. |
| D840,534 S | 2/2019 | Mozzicato et al. |
| 10,225,376 B2 | 3/2019 | Perez Martinez |
| 10,226,376 B2 | 3/2019 | Sanchez et al. |
| D848,612 S | 5/2019 | Mozzicato et al. |
| 10,307,305 B1 | 6/2019 | Hodges |
| 10,335,121 B2 | 7/2019 | Desai |
| D856,512 S | 8/2019 | Cowart et al. |
| 10,376,406 B2 | 8/2019 | Newton |
| 10,376,407 B2 | 8/2019 | Newton |
| 10,390,989 B2 | 8/2019 | Sanchez et al. |
| D858,144 S | 9/2019 | Fu |
| 10,406,039 B2 | 9/2019 | Villarreal |
| 10,407,222 B2 | 9/2019 | Allen |
| 10,478,356 B2 | 11/2019 | Griffin |
| 10,538,366 B2 | 1/2020 | Pentelovitch et al. |
| 10,569,938 B2 | 2/2020 | Zhao et al. |
| 10,577,156 B2 | 3/2020 | Dagnelie et al. |
| 10,618,721 B2 | 4/2020 | Vazin |
| D884,390 S | 5/2020 | Wang |
| 10,669,079 B2 | 6/2020 | Freedman et al. |
| D892,315 S | 8/2020 | Airy |
| 10,730,672 B2 | 8/2020 | Bertram et al. |
| 10,737,848 B2 | 8/2020 | Philip et al. |
| 10,765,854 B2 | 9/2020 | Law et al. |
| 10,766,670 B2 | 9/2020 | Kittmann |
| 10,799,386 B1 | 10/2020 | Harrison |
| D901,214 S | 11/2020 | Hu |
| 10,857,025 B2 | 12/2020 | Davis et al. |
| 10,865,017 B1 | 12/2020 | Cowart et al. |
| 10,889,412 B2 | 1/2021 | West et al. |
| 10,913,581 B2 | 2/2021 | Stahlecker |
| D912,244 S | 3/2021 | Rehm et al. |
| 10,952,889 B2 | 3/2021 | Newton et al. |
| 10,973,678 B2 | 4/2021 | Newton et al. |
| 10,974,874 B2 | 4/2021 | Ragias et al. |
| 11,000,401 B2 | 5/2021 | Ecklund et al. |
| D923,365 S | 6/2021 | Wang |
| 11,026,829 B2 | 6/2021 | Harvie |
| 11,027,900 B2 | 6/2021 | Liu |
| 11,045,346 B2 | 6/2021 | Argent et al. |
| D928,946 S | 8/2021 | Sanchez et al. |
| 11,179,506 B2 | 11/2021 | Barr et al. |

(56) References Cited

U.S. PATENT DOCUMENTS

| | | |
|---|---|---|
| 11,226,376 B2 | 1/2022 | Yamauchi et al. |
| 11,376,152 B2 | 7/2022 | Sanchez et al. |
| 11,382,786 B2 | 7/2022 | Sanchez et al. |
| 11,382,788 B2 | 7/2022 | Hjorth et al. |
| 11,426,303 B2 | 8/2022 | Davis et al. |
| 11,529,252 B2 | 12/2022 | Glithero et al. |
| 2001/0037097 A1 | 11/2001 | Cheng et al. |
| 2001/0054426 A1 | 12/2001 | Knudson et al. |
| 2002/0019614 A1 | 2/2002 | Woon |
| 2002/0026161 A1 | 2/2002 | Grundke |
| 2002/0087131 A1 | 7/2002 | Wolff et al. |
| 2002/0091364 A1 | 7/2002 | Prabhakar |
| 2002/0189992 A1 | 12/2002 | Schmidt et al. |
| 2002/0193760 A1 | 12/2002 | Thompson |
| 2003/0004436 A1 | 1/2003 | Schmidt et al. |
| 2003/0032931 A1 | 2/2003 | Grundke et al. |
| 2003/0120178 A1 | 6/2003 | Heki |
| 2003/0157859 A1 | 8/2003 | Ishikawa |
| 2003/0181880 A1 | 9/2003 | Schwartz |
| 2003/0195484 A1 | 10/2003 | Harvie |
| 2003/0204173 A1 | 10/2003 | Burns et al. |
| 2003/0233079 A1 | 12/2003 | Parks et al. |
| 2004/0006321 A1 | 1/2004 | Cheng et al. |
| 2004/0056122 A1 | 3/2004 | Male et al. |
| 2004/0084465 A1 | 5/2004 | Luburic |
| 2004/0127872 A1 | 7/2004 | Petryk et al. |
| 2004/0128749 A1 | 7/2004 | Scott |
| 2004/0143229 A1 | 7/2004 | Easter |
| 2004/0147894 A1 | 7/2004 | Mizutani et al. |
| 2004/0158221 A1 | 8/2004 | Mizutani et al. |
| 2004/0176731 A1 | 9/2004 | Cheng et al. |
| 2004/0176746 A1 | 9/2004 | Forral |
| 2004/0191919 A1 | 9/2004 | Unger et al. |
| 2004/0207530 A1 | 10/2004 | Nielsen |
| 2004/0236292 A1 | 11/2004 | Tazoe et al. |
| 2004/0254547 A1 | 12/2004 | Okabe et al. |
| 2005/0010182 A1 | 1/2005 | Parks et al. |
| 2005/0033248 A1 | 2/2005 | Machida et al. |
| 2005/0065471 A1 | 3/2005 | Kuntz |
| 2005/0070861 A1 | 3/2005 | Okabe et al. |
| 2005/0070862 A1 | 3/2005 | Tazoe et al. |
| 2005/0082300 A1 | 4/2005 | Modrell et al. |
| 2005/0097662 A1 | 5/2005 | Leimkuhler et al. |
| 2005/0101924 A1 | 5/2005 | Elson et al. |
| 2005/0137557 A1 | 6/2005 | Swiecicki et al. |
| 2005/0154360 A1 | 7/2005 | Harvie |
| 2005/0177070 A1 | 8/2005 | Levinson et al. |
| 2005/0197639 A1 | 9/2005 | Mombrinie |
| 2005/0273920 A1 | 12/2005 | Marinas |
| 2005/0277904 A1 | 12/2005 | Chase et al. |
| 2005/0279359 A1 | 12/2005 | Leblanc et al. |
| 2006/0004332 A1 | 1/2006 | Marx |
| 2006/0015080 A1 | 1/2006 | Mahnensmith |
| 2006/0015081 A1 | 1/2006 | Suzuki et al. |
| 2006/0016778 A1 | 1/2006 | Park |
| 2006/0079854 A1 | 4/2006 | Kay et al. |
| 2006/0111648 A1 | 5/2006 | Vermaak |
| 2006/0155214 A1 | 7/2006 | Wightman |
| 2006/0200102 A1 | 9/2006 | Cooper |
| 2006/0229575 A1 | 10/2006 | Boiarski |
| 2006/0229576 A1 | 10/2006 | Conway et al. |
| 2006/0231648 A1 | 10/2006 | Male et al. |
| 2006/0235266 A1 | 10/2006 | Nan |
| 2006/0235359 A1 | 10/2006 | Marland |
| 2006/0269439 A1 | 11/2006 | White |
| 2006/0277670 A1 | 12/2006 | Baker et al. |
| 2007/0006368 A1 | 1/2007 | Key et al. |
| 2007/0010797 A1* | 1/2007 | Nishtala .............. A61B 5/208 604/540 |
| 2007/0016152 A1 | 1/2007 | Karpowicz et al. |
| 2007/0038194 A1 | 2/2007 | Wada et al. |
| 2007/0055209 A1 | 3/2007 | Patel et al. |
| 2007/0073252 A1 | 3/2007 | Forgrave |
| 2007/0117880 A1 | 5/2007 | Elson et al. |
| 2007/0135786 A1 | 6/2007 | Schmidt et al. |
| 2007/0149935 A1 | 6/2007 | Dirico |
| 2007/0191804 A1 | 8/2007 | Coley |
| 2007/0214553 A1 | 9/2007 | Carromba et al. |
| 2007/0225663 A1 | 9/2007 | Watt et al. |
| 2007/0225666 A1 | 9/2007 | Otto |
| 2007/0225668 A1 | 9/2007 | Otto |
| 2007/0266486 A1 | 11/2007 | Ramirez |
| 2007/0282309 A1 | 12/2007 | Bengtson et al. |
| 2008/0004576 A1 | 1/2008 | Tanaka et al. |
| 2008/0015526 A1 | 1/2008 | Reiner et al. |
| 2008/0015527 A1 | 1/2008 | House |
| 2008/0033386 A1 | 2/2008 | Okabe et al. |
| 2008/0041869 A1 | 2/2008 | Backaert |
| 2008/0091153 A1 | 4/2008 | Harvie |
| 2008/0091158 A1 | 4/2008 | Yang |
| 2008/0167634 A1 | 7/2008 | Kouta et al. |
| 2008/0183157 A1 | 7/2008 | Walters |
| 2008/0215031 A1 | 9/2008 | Belfort et al. |
| 2008/0234642 A1 | 9/2008 | Patterson et al. |
| 2008/0281282 A1 | 11/2008 | Finger et al. |
| 2008/0287894 A1 | 11/2008 | Van Den Heuvel et al. |
| 2009/0025717 A1 | 1/2009 | Pinel |
| 2009/0048570 A1 | 2/2009 | Jensen |
| 2009/0056003 A1 | 3/2009 | Ivie et al. |
| 2009/0069761 A1 | 3/2009 | Vogel |
| 2009/0069765 A1 | 3/2009 | Wortham |
| 2009/0192482 A1 | 7/2009 | Dodge et al. |
| 2009/0234312 A1 | 9/2009 | Otoole et al. |
| 2009/0251510 A1 | 10/2009 | Noro et al. |
| 2009/0264840 A1 | 10/2009 | Virginio |
| 2009/0270822 A1 | 10/2009 | Medeiros |
| 2009/0281510 A1 | 11/2009 | Fisher |
| 2010/0004612 A1 | 1/2010 | Thevenin |
| 2010/0058660 A1 | 3/2010 | Williams |
| 2010/0121289 A1 | 5/2010 | Parks et al. |
| 2010/0158168 A1 | 6/2010 | Murthy et al. |
| 2010/0185168 A1 | 7/2010 | Graauw et al. |
| 2010/0198172 A1 | 8/2010 | Wada et al. |
| 2010/0211032 A1 | 8/2010 | Tsai et al. |
| 2010/0234820 A1 | 9/2010 | Tsai et al. |
| 2010/0241104 A1 | 9/2010 | Gilbert |
| 2010/0263113 A1 | 10/2010 | Shelton et al. |
| 2010/0310845 A1 | 12/2010 | Bond et al. |
| 2011/0028920 A1 | 2/2011 | Johannison |
| 2011/0028922 A1 | 2/2011 | Kay et al. |
| 2011/0034889 A1 | 2/2011 | Smith |
| 2011/0036837 A1 | 2/2011 | Shang |
| 2011/0040267 A1 | 2/2011 | Wada et al. |
| 2011/0040271 A1 | 2/2011 | Rogers et al. |
| 2011/0054426 A1 | 3/2011 | Stewart et al. |
| 2011/0060300 A1 | 3/2011 | Weig et al. |
| 2011/0077495 A1 | 3/2011 | Gilbert |
| 2011/0077606 A1 | 3/2011 | Wilcox et al. |
| 2011/0087337 A1 | 4/2011 | Forsell |
| 2011/0137273 A1 | 6/2011 | Muellejans et al. |
| 2011/0145993 A1 | 6/2011 | Rader et al. |
| 2011/0152802 A1 | 6/2011 | Dicamillo et al. |
| 2011/0164147 A1 | 7/2011 | Takahashi et al. |
| 2011/0172620 A1 | 7/2011 | Khambatta |
| 2011/0172625 A1 | 7/2011 | Wada et al. |
| 2011/0202024 A1 | 8/2011 | Cozzens |
| 2011/0238023 A1 | 9/2011 | Slayton |
| 2011/0240648 A1 | 10/2011 | Tucker |
| 2011/0251572 A1 | 10/2011 | Nishtala et al. |
| 2011/0265889 A1 | 11/2011 | Tanaka et al. |
| 2011/0276020 A1 | 11/2011 | Mitsui |
| 2012/0035577 A1 | 2/2012 | Tomes et al. |
| 2012/0041400 A1 | 2/2012 | Christensen |
| 2012/0059328 A1 | 3/2012 | Dikeman et al. |
| 2012/0066825 A1 | 3/2012 | Birbara et al. |
| 2012/0103347 A1 | 5/2012 | Wheaton et al. |
| 2012/0137420 A1 | 6/2012 | Gordon et al. |
| 2012/0165768 A1 | 6/2012 | Sekiyama et al. |
| 2012/0165786 A1 | 6/2012 | Chappa et al. |
| 2012/0210503 A1 | 8/2012 | Anzivino et al. |
| 2012/0233761 A1 | 9/2012 | Huang |
| 2012/0245541 A1 | 9/2012 | Suzuki et al. |
| 2012/0245542 A1 | 9/2012 | Suzuki et al. |
| 2012/0245547 A1 | 9/2012 | Wilcox et al. |

(56) References Cited

U.S. PATENT DOCUMENTS

| | | |
|---|---|---|
| 2012/0253303 A1 | 10/2012 | Suzuki et al. |
| 2012/0271259 A1 | 10/2012 | Ulert |
| 2012/0296305 A1 | 11/2012 | Barraza Khaled et al. |
| 2012/0316522 A1 | 12/2012 | Carter et al. |
| 2012/0330256 A1 | 12/2012 | Wilcox et al. |
| 2013/0006206 A1 | 1/2013 | Wada et al. |
| 2013/0045651 A1 | 2/2013 | Esteves et al. |
| 2013/0053804 A1 | 2/2013 | Soerensen et al. |
| 2013/0096523 A1 | 4/2013 | Chang et al. |
| 2013/0150813 A1 | 6/2013 | Gordon et al. |
| 2013/0245496 A1 | 9/2013 | Wells et al. |
| 2013/0245586 A1 | 9/2013 | Jha |
| 2013/0292537 A1 | 11/2013 | Dirico |
| 2014/0031774 A1 | 1/2014 | Bengtson |
| 2014/0157499 A1 | 6/2014 | Suzuki et al. |
| 2014/0171889 A1 | 6/2014 | Hopman et al. |
| 2014/0182051 A1 | 7/2014 | Tanimoto et al. |
| 2014/0196189 A1 | 7/2014 | Lee et al. |
| 2014/0276501 A1 | 9/2014 | Cisko |
| 2014/0303582 A1 | 10/2014 | Wright et al. |
| 2014/0316381 A1 | 10/2014 | Reglin |
| 2014/0325746 A1 | 11/2014 | Block |
| 2014/0348139 A1 | 11/2014 | Gomez Martinez |
| 2014/0352050 A1 | 12/2014 | Yao et al. |
| 2014/0371628 A1 | 12/2014 | Desai |
| 2015/0045757 A1 | 2/2015 | Lee et al. |
| 2015/0047114 A1 | 2/2015 | Ramirez |
| 2015/0048089 A1 | 2/2015 | Robertson |
| 2015/0135423 A1 | 5/2015 | Sharpe et al. |
| 2015/0157300 A1 | 6/2015 | Ealovega et al. |
| 2015/0209194 A1 | 7/2015 | Heyman |
| 2015/0290425 A1 | 10/2015 | Macy et al. |
| 2015/0320583 A1 | 11/2015 | Harvie |
| 2015/0329255 A1 | 11/2015 | Rzepecki |
| 2015/0359660 A1 | 12/2015 | Harvie |
| 2015/0366699 A1 | 12/2015 | Nelson |
| 2016/0029998 A1 | 2/2016 | Brister et al. |
| 2016/0030228 A1 | 2/2016 | Jones |
| 2016/0038356 A1 | 2/2016 | Yao et al. |
| 2016/0058322 A1 | 3/2016 | Brister et al. |
| 2016/0060001 A1 | 3/2016 | Wada et al. |
| 2016/0100976 A1 | 4/2016 | Conway et al. |
| 2016/0106604 A1 | 4/2016 | Timm |
| 2016/0113809 A1 | 4/2016 | Kim |
| 2016/0183689 A1 | 6/2016 | Miner |
| 2016/0256022 A1 | 9/2016 | Le |
| 2016/0270982 A1 | 9/2016 | Raycheck et al. |
| 2016/0278662 A1 | 9/2016 | Brister et al. |
| 2016/0357400 A1 | 12/2016 | Penha et al. |
| 2016/0366699 A1 | 12/2016 | Zhang et al. |
| 2016/0367226 A1 | 12/2016 | Newton et al. |
| 2016/0367411 A1 | 12/2016 | Justiz et al. |
| 2016/0374848 A1 | 12/2016 | Sanchez et al. |
| 2017/0007438 A1 | 1/2017 | Harvie |
| 2017/0014560 A1 | 1/2017 | Minskoff et al. |
| 2017/0100276 A1 | 4/2017 | Joh |
| 2017/0128638 A1 | 5/2017 | Giezendanner et al. |
| 2017/0143534 A1 | 5/2017 | Sanchez |
| 2017/0165405 A1 | 6/2017 | Muser et al. |
| 2017/0189225 A1 | 7/2017 | Voorhees et al. |
| 2017/0202692 A1 | 7/2017 | Laniado |
| 2017/0216081 A1 | 8/2017 | Accosta |
| 2017/0246026 A1 | 8/2017 | Laniado |
| 2017/0252014 A1 | 9/2017 | Siller Gonzalez et al. |
| 2017/0252202 A9 | 9/2017 | Sanchez et al. |
| 2017/0266031 A1 | 9/2017 | Sanchez et al. |
| 2017/0266658 A1 | 9/2017 | Bruno et al. |
| 2017/0281399 A1 | 10/2017 | Vanmiddendorp et al. |
| 2017/0312116 A1 | 11/2017 | Laniado |
| 2017/0325788 A1 | 11/2017 | Ealovega et al. |
| 2017/0333244 A1 | 11/2017 | Laniado |
| 2017/0042748 A1 | 12/2017 | Griffin |
| 2017/0348139 A1 | 12/2017 | Newton et al. |
| 2017/0354532 A1 | 12/2017 | Holt |
| 2017/0367873 A1 | 12/2017 | Grannum |
| 2018/0002075 A1 | 1/2018 | Lee |
| 2018/0008451 A1 | 1/2018 | Stroebech |
| 2018/0008804 A1 | 1/2018 | Laniado |
| 2018/0021218 A1 | 1/2018 | Brosch et al. |
| 2018/0028349 A1 | 2/2018 | Newton et al. |
| 2018/0037384 A1 | 2/2018 | Archeny et al. |
| 2018/0049910 A1 | 2/2018 | Newton |
| 2018/0064572 A1 | 3/2018 | Wiltshire |
| 2018/0104131 A1 | 4/2018 | Killian |
| 2018/0127187 A1 | 5/2018 | Sewell |
| 2018/0193215 A1 | 7/2018 | Davies et al. |
| 2018/0200101 A1 | 7/2018 | Su |
| 2018/0228642 A1 | 8/2018 | Davis et al. |
| 2018/0256384 A1 | 9/2018 | Kasirye |
| 2018/0271694 A1 | 9/2018 | Fernandez et al. |
| 2018/0317892 A1 | 11/2018 | Catlin |
| 2019/0001030 A1 | 1/2019 | Braga et al. |
| 2019/0021899 A1 | 1/2019 | Vlet |
| 2019/0038451 A1 | 2/2019 | Harvie |
| 2019/0046102 A1 | 2/2019 | Kushnir et al. |
| 2019/0100362 A1 | 4/2019 | Meyers et al. |
| 2019/0133814 A1 | 5/2019 | Tammen et al. |
| 2019/0142624 A1 | 5/2019 | Sanchez et al. |
| 2019/0224036 A1 | 7/2019 | Sanchez et al. |
| 2019/0247222 A1 | 8/2019 | Ecklund et al. |
| 2019/0247223 A1 | 8/2019 | Brun et al. |
| 2019/0282391 A1 | 9/2019 | Johannes et al. |
| 2019/0314189 A1 | 10/2019 | Acosta |
| 2019/0314190 A1 | 10/2019 | Sanchez et al. |
| 2019/0321587 A1 | 10/2019 | Mcmenamin et al. |
| 2019/0344934 A1 | 11/2019 | Faerber et al. |
| 2019/0365307 A1 | 12/2019 | Laing et al. |
| 2019/0365561 A1 | 12/2019 | Newton et al. |
| 2020/0008985 A1 | 1/2020 | Nguyen et al. |
| 2020/0030595 A1 | 1/2020 | Boukidjian et al. |
| 2020/0046544 A1 | 2/2020 | Godinez et al. |
| 2020/0055638 A1 | 2/2020 | Lau et al. |
| 2020/0070392 A1 | 3/2020 | Huber et al. |
| 2020/0085609 A1 | 3/2020 | Schelch et al. |
| 2020/0085610 A1 | 3/2020 | Cohn et al. |
| 2020/0086090 A1 | 3/2020 | Von Weymarn-schärli et al. |
| 2020/0129322 A1 | 4/2020 | Leuckel |
| 2020/0171217 A9 | 6/2020 | Braga et al. |
| 2020/0229964 A1 | 7/2020 | Staali et al. |
| 2020/0231343 A1 | 7/2020 | Freedman et al. |
| 2020/0232841 A1 | 7/2020 | Satish et al. |
| 2020/0246172 A1 | 8/2020 | Ho |
| 2020/0255189 A1 | 8/2020 | Liu |
| 2020/0261280 A1 | 8/2020 | Heyman |
| 2020/0276046 A1 | 9/2020 | Staali et al. |
| 2020/0306075 A1 | 10/2020 | Newton et al. |
| 2020/0315838 A1 | 10/2020 | Eckert |
| 2020/0331672 A1 | 10/2020 | Bertram et al. |
| 2020/0345332 A1 | 11/2020 | Duval |
| 2020/0353135 A1 | 11/2020 | Gregory et al. |
| 2020/0367677 A1 | 11/2020 | Silsby et al. |
| 2020/0369444 A1 | 11/2020 | Silsby et al. |
| 2020/0375781 A1 | 12/2020 | Staali et al. |
| 2020/0385179 A1 | 12/2020 | McCourt |
| 2020/0390591 A1 | 12/2020 | Glithero et al. |
| 2020/0390592 A1 | 12/2020 | Merrill |
| 2020/0405521 A1 | 12/2020 | Glasroe |
| 2021/0008771 A1 | 1/2021 | Huber et al. |
| 2021/0009323 A1 | 1/2021 | Markarian et al. |
| 2021/0059853 A1 | 3/2021 | Davis et al. |
| 2021/0061523 A1 | 3/2021 | Bytheway |
| 2021/0069005 A1 | 3/2021 | Sanchez et al. |
| 2021/0069008 A1 | 3/2021 | Blabas et al. |
| 2021/0077993 A1 | 3/2021 | Nazareth et al. |
| 2021/0113749 A1 | 4/2021 | Radl et al. |
| 2021/0121318 A1 | 4/2021 | Pinlac |
| 2021/0137724 A1 | 5/2021 | Ecklund et al. |
| 2021/0138190 A1* | 5/2021 | Erbey, II ............ A61M 1/743 |
| 2021/0154055 A1 | 5/2021 | Villarreal |
| 2021/0170079 A1 | 6/2021 | Radl et al. |
| 2021/0220162 A1 | 7/2021 | Jamison |
| 2021/0220163 A1 | 7/2021 | Mayrand |
| 2021/0228400 A1 | 7/2021 | Glithero |
| 2021/0228401 A1 | 7/2021 | Becker et al. |

(56) References Cited

U.S. PATENT DOCUMENTS

| | | | |
|---|---|---|---|
| 2021/0228795 A1 | 7/2021 | Hughett et al. |
| 2021/0229877 A1 | 7/2021 | Ragias et al. |
| 2021/0236323 A1 | 8/2021 | Austermann et al. |
| 2021/0267787 A1 | 9/2021 | Nazemi |
| 2021/0275343 A1 | 9/2021 | Sanchez et al. |
| 2021/0315727 A1 | 10/2021 | Jiang |
| 2021/0353450 A1 | 11/2021 | Sharma et al. |
| 2021/0361469 A1 | 11/2021 | Liu et al. |
| 2021/0369495 A1 | 12/2021 | Cheng et al. |
| 2021/0386925 A1 | 12/2021 | Hartwell et al. |
| 2021/0393433 A1 | 12/2021 | Godinez et al. |
| 2022/0023091 A1 | 1/2022 | Ecklund et al. |
| 2022/0047410 A1 | 2/2022 | Walthall |
| 2022/0062027 A1 | 3/2022 | Mitchell et al. |
| 2022/0062028 A1 | 3/2022 | Mitchell et al. |
| 2022/0062029 A1 | 3/2022 | Johannes et al. |
| 2022/0066825 A1 | 3/2022 | Saraf et al. |
| 2022/0071811 A1 | 3/2022 | Cheng et al. |
| 2022/0071826 A1 | 3/2022 | Kulkarni et al. |
| 2022/0104965 A1 | 4/2022 | Vaninetti et al. |
| 2022/0104981 A1 | 4/2022 | Jones |
| 2022/0117774 A1 | 4/2022 | Meyer et al. |
| 2022/0117775 A1 | 4/2022 | Jones et al. |
| 2022/0133524 A1 | 5/2022 | Davis |
| 2022/0151817 A1 | 5/2022 | Mann |
| 2022/0160949 A1* | 5/2022 | Simiele ............... A61M 1/804 |
| 2022/0211536 A1 | 7/2022 | Johannes et al. |
| 2022/0218510 A1 | 7/2022 | Metzger et al. |
| 2022/0229053 A1 | 7/2022 | Levin et al. |
| 2022/0248836 A1 | 8/2022 | Cagle et al. |
| 2022/0257407 A1 | 8/2022 | Johannes et al. |
| 2022/0265462 A1 | 8/2022 | Alder et al. |
| 2022/0273482 A1 | 9/2022 | Johannes et al. |
| 2022/0280357 A1 | 9/2022 | Jagannathan et al. |
| 2022/0313222 A1 | 10/2022 | Austermann et al. |
| 2022/0313474 A1 | 10/2022 | Kriscovich et al. |
| 2022/0354685 A1 | 11/2022 | Davis et al. |
| 2022/0370231 A1 | 11/2022 | Wang et al. |
| 2022/0370234 A1 | 11/2022 | Hughett et al. |
| 2022/0370235 A1 | 11/2022 | Johannes et al. |
| 2022/0370237 A1 | 11/2022 | Parmar et al. |
| 2022/0387001 A1 | 12/2022 | Askenazi et al. |
| 2022/0395391 A1 | 12/2022 | Saunders et al. |
| 2023/0018845 A1 | 1/2023 | Lee |
| 2023/0020563 A1 | 1/2023 | Sharma et al. |
| 2023/0031640 A1 | 2/2023 | Hughett et al. |
| 2023/0037159 A1 | 2/2023 | Brennan et al. |
| 2023/0062994 A1 | 3/2023 | Ecklund et al. |
| 2023/0089032 A1 | 3/2023 | Hughett et al. |
| 2023/0105001 A1 | 4/2023 | Whittome et al. |
| 2023/0138269 A1 | 5/2023 | Abdelal et al. |
| 2023/0145365 A1 | 5/2023 | Martin et al. |
| 2023/0277362 A1 | 9/2023 | Davis et al. |

FOREIGN PATENT DOCUMENTS

| | | | | |
|---|---|---|---|---|
| CA | 2354132 A1 | 6/2000 | | |
| CA | 2488867 C | 8/2007 | | |
| CA | 3050918 A1 | 8/2018 | | |
| CA | 3098571 A1 | 11/2019 | | |
| CN | 2269203 Y | 12/1997 | | |
| CN | 1332620 A | 1/2002 | | |
| CN | 1533755 A | 10/2004 | | |
| CN | 1602825 A | 4/2005 | | |
| CN | 1720888 A | 1/2006 | | |
| CN | 2936204 Y | 8/2007 | | |
| CN | 101262836 A | 9/2008 | | |
| CN | 101522148 A | 9/2009 | | |
| CN | 102159159 A | 8/2011 | | |
| CN | 202184840 U | 4/2012 | | |
| CN | 102481441 A | 5/2012 | | |
| CN | 202463712 U | 10/2012 | | |
| CN | 103533968 A | 1/2014 | | |
| CN | 103717180 A | 4/2014 | | |
| CN | 204562697 U | 8/2015 | | |
| CN | 105451693 A | 3/2016 | | |
| CN | 205849719 U | 1/2017 | | |
| CN | 107847384 A | 3/2018 | | |
| CN | 107920912 A | 4/2018 | | |
| CN | 209285902 U | 8/2019 | | |
| CN | 110381883 A | * 10/2019 | ............... | A61D 1/00 |
| CN | 211198839 U | 8/2020 | | |
| CN | 112566550 A | * 3/2021 | ........... | A61B 5/0004 |
| CN | 112603184 A | * 4/2021 | ........... | A61B 10/007 |
| CN | 114007493 A | * 2/2022 | ......... | A61B 5/10362 |
| CN | 114375187 A | 4/2022 | | |
| CN | 116096332 A | 5/2023 | | |
| DE | 79818 C | 10/1893 | | |
| DE | 1516466 A1 | 6/1969 | | |
| DE | 2721330 A1 | 11/1977 | | |
| DE | 2742298 A1 | 3/1978 | | |
| DE | 9407554.9 U1 | 5/1995 | | |
| DE | 4443710 A1 | 6/1995 | | |
| DE | 19619597 A1 | 11/1997 | | |
| DE | 102011103783 A1 | 12/2012 | | |
| DE | 202015104597 U1 | 7/2016 | | |
| DK | 9600118 | 11/1996 | | |
| EP | 0032138 A2 | 7/1981 | | |
| EP | 0066070 B1 | 12/1982 | | |
| EP | 0274753 A2 | 7/1988 | | |
| EP | 0119143 B1 | 11/1988 | | |
| EP | 0610638 A1 | 8/1994 | | |
| EP | 0613355 A1 | 9/1994 | | |
| EP | 0613355 B1 | 1/1997 | | |
| EP | 0787472 A1 | 8/1997 | | |
| EP | 0966936 A1 | 12/1999 | | |
| EP | 0987293 A1 | 3/2000 | | |
| EP | 1063953 A1 | 1/2001 | | |
| EP | 0653928 B1 | 10/2002 | | |
| EP | 1332738 A1 | 8/2003 | | |
| EP | 1382318 A1 | 1/2004 | | |
| EP | 1089684 B1 | 10/2004 | | |
| EP | 1616542 A1 | 1/2006 | | |
| EP | 1382318 B1 | 5/2006 | | |
| EP | 1063953 B1 | 1/2007 | | |
| EP | 1872752 A1 | 1/2008 | | |
| EP | 2180907 A1 | 5/2010 | | |
| EP | 2380532 A1 | 10/2011 | | |
| EP | 2389908 A1 | 11/2011 | | |
| EP | 2601916 A1 | 6/2013 | | |
| EP | 2676643 A1 | 12/2013 | | |
| EP | 2997950 A2 | 3/2016 | | |
| EP | 2879534 B1 | 3/2017 | | |
| EP | 3424471 A1 | 1/2019 | | |
| EP | 3169292 B1 | 11/2019 | | |
| EP | 3753492 A1 | * 12/2020 | ........... | A61B 10/007 |
| EP | 3788992 A1 | 3/2021 | | |
| EP | 3576689 B1 | 3/2022 | | |
| EP | 3752110 B1 | 3/2022 | | |
| EP | 4025163 A1 | 7/2022 | | |
| GB | 1011517 A | 12/1965 | | |
| GB | 1467144 A | 3/1977 | | |
| GB | 2106395 A | 4/1983 | | |
| GB | 2106784 A | 4/1983 | | |
| GB | 2148126 A | 5/1985 | | |
| GB | 2171315 A | 8/1986 | | |
| GB | 2148126 B | 7/1987 | | |
| GB | 2191095 A | 12/1987 | | |
| GB | 2199750 A | 7/1988 | | |
| GB | 2260907 A | 5/1993 | | |
| GB | 2462267 A | 2/2010 | | |
| GB | 2469496 A | 10/2010 | | |
| GB | 2490327 A | 10/2012 | | |
| GB | 2507318 A | 4/2014 | | |
| IT | 201800009129 A1 | 4/2020 | | |
| JP | S5410596 A | 1/1979 | | |
| JP | S5410596 Y2 | 5/1979 | | |
| JP | S55155618 A | 12/1980 | | |
| JP | S5888596 U | 6/1983 | | |
| JP | S63107780 U | 7/1988 | | |
| JP | H0267530 A | 3/1990 | | |
| JP | H02103871 A | 4/1990 | | |
| JP | H02131422 A | 5/1990 | | |
| JP | H02131422 U | 11/1990 | | |

(56) References Cited

FOREIGN PATENT DOCUMENTS

| | | |
|---|---|---|
| JP | H0460220 A | 2/1992 |
| JP | H05123349 A | 5/1993 |
| JP | H05123350 A | 5/1993 |
| JP | 3087938 B2 | 10/1995 |
| JP | H085630 A | 1/1996 |
| JP | H1040141 A | 2/1998 |
| JP | H10225430 A | 8/1998 |
| JP | H11113946 A | 4/1999 |
| JP | H11290365 A | 10/1999 |
| JP | 2000116690 A | 4/2000 |
| JP | 2000185068 A | 7/2000 |
| JP | 2001054531 A | 2/2001 |
| JP | 2001070331 A | 3/2001 |
| JP | 2001224616 A | 8/2001 |
| JP | 2001276107 A | 10/2001 |
| JP | 2001276108 A | 10/2001 |
| JP | 2002028173 A | 1/2002 |
| JP | 2003505152 A | 2/2003 |
| JP | 2003180722 A | 7/2003 |
| JP | 2004130056 A | 4/2004 |
| JP | 2004267530 A | 9/2004 |
| JP | 2005066011 A | 3/2005 |
| JP | 2005066325 A | 3/2005 |
| JP | 2005518237 A | 6/2005 |
| JP | 3749097 B2 | 12/2005 |
| JP | 2006026108 A | 2/2006 |
| JP | 3123547 B2 | 6/2006 |
| JP | 2006136492 A | 6/2006 |
| JP | 2006204868 A | 8/2006 |
| JP | 2007044494 A | 2/2007 |
| JP | 3132659 B2 | 5/2007 |
| JP | 4039641 B2 | 11/2007 |
| JP | 2009509570 A | 3/2009 |
| JP | 2010081981 A | 4/2010 |
| JP | 4640772 B2 | 12/2010 |
| JP | 2010536439 A | 12/2010 |
| JP | 4747166 B2 | 5/2011 |
| JP | 2011087823 A | 5/2011 |
| JP | 4801218 B1 | 8/2011 |
| JP | 2011218130 A | 11/2011 |
| JP | 2011224070 A | 11/2011 |
| JP | 2012523869 A | 10/2012 |
| JP | 2013238608 A | 11/2013 |
| JP | 2014521960 A | 8/2014 |
| JP | 2015092945 A | 5/2015 |
| JP | 3198994 B2 | 7/2015 |
| JP | 2019525811 A | 9/2019 |
| JP | 2021120686 A | 8/2021 |
| JP | 2021522009 A | 8/2021 |
| JP | 7129493 B2 | 8/2022 |
| JP | 2023532132 A | 7/2023 |
| KR | 200290061 Y1 | 9/2002 |
| KR | 20030047451 A | 6/2003 |
| KR | 20140039485 A | 4/2014 |
| KR | 101432639 B1 | 8/2014 |
| KR | 20180106659 A | 10/2018 |
| KR | 20180108774 A | 10/2018 |
| PT | 2068717 E | 6/2013 |
| WO | 8101957 A1 | 7/1981 |
| WO | 8804558 A1 | 6/1988 |
| WO | 9104714 A2 | 4/1991 |
| WO | 9104714 A3 | 6/1991 |
| WO | 9220299 A3 | 2/1993 |
| WO | 9307839 A1 | 4/1993 |
| WO | 9309736 A2 | 5/1993 |
| WO | 9309736 A3 | 6/1993 |
| WO | 9514448 A2 | 6/1995 |
| WO | 9600096 A1 | 1/1996 |
| WO | 9634636 A1 | 11/1996 |
| WO | 9817211 A1 | 4/1998 |
| WO | 9830336 A1 | 7/1998 |
| WO | 0000112 A1 | 1/2000 |
| WO | 0000113 A1 | 1/2000 |
| WO | 0025651 A1 | 5/2000 |
| WO | 0033773 A1 | 6/2000 |
| WO | 0057784 A1 | 10/2000 |
| WO | 0069377 A1 | 11/2000 |
| WO | 0145618 A1 | 6/2001 |
| WO | 0145621 A1 | 6/2001 |
| WO | 02094160 A1 | 11/2002 |
| WO | 03013967 A1 | 2/2003 |
| WO | 03024824 A1 | 3/2003 |
| WO | WO-03055423 A1 * | 7/2003 ........... A61F 5/4405 |
| WO | 03071931 A2 | 9/2003 |
| WO | 03079942 A1 | 10/2003 |
| WO | 03071931 A3 | 2/2004 |
| WO | 2004019836 A1 | 3/2004 |
| WO | 2004024046 A1 | 3/2004 |
| WO | 2005074571 A3 | 9/2005 |
| WO | 2005089687 A2 | 9/2005 |
| WO | 2005107661 A2 | 11/2005 |
| WO | 2006021220 A1 | 3/2006 |
| WO | WO-2006037140 A2 * | 4/2006 ......... A61B 10/0051 |
| WO | 2007007845 A1 | 1/2007 |
| WO | WO-2007005851 A2 * | 1/2007 ......... A61B 5/14507 |
| WO | 2007042823 A2 | 4/2007 |
| WO | 2007055651 A1 | 5/2007 |
| WO | 2006098950 A3 | 11/2007 |
| WO | 2007134608 A2 | 11/2007 |
| WO | 2007128156 A3 | 2/2008 |
| WO | 2008026106 A2 | 3/2008 |
| WO | 2008078117 A1 | 7/2008 |
| WO | 2008104019 A1 | 9/2008 |
| WO | 2008141471 A1 | 11/2008 |
| WO | 2009004368 A1 | 1/2009 |
| WO | 2009004369 A1 | 1/2009 |
| WO | 2009052496 A1 | 4/2009 |
| WO | 2009052502 A1 | 4/2009 |
| WO | 2009007702 A4 | 7/2009 |
| WO | 2009101738 A1 | 8/2009 |
| WO | 2010058192 A1 | 5/2010 |
| WO | 2010030122 A3 | 7/2010 |
| WO | 2010101915 A3 | 1/2011 |
| WO | 2011018132 A1 | 2/2011 |
| WO | 2011018133 A1 | 2/2011 |
| WO | 2011024864 A1 | 3/2011 |
| WO | 2011054118 A1 | 5/2011 |
| WO | 2011079132 A1 | 6/2011 |
| WO | 2011107972 A1 | 9/2011 |
| WO | 2011108972 A1 | 9/2011 |
| WO | 2011117292 A1 | 9/2011 |
| WO | 2011123219 A1 | 10/2011 |
| WO | 2011132043 A1 | 10/2011 |
| WO | 2012012908 A1 | 2/2012 |
| WO | 2012065274 A1 | 5/2012 |
| WO | 2012097462 A1 | 7/2012 |
| WO | 2012098796 A1 | 7/2012 |
| WO | 2012101288 A1 | 8/2012 |
| WO | 2012175916 A1 | 12/2012 |
| WO | 2013018435 A1 | 2/2013 |
| WO | 2013033429 A1 | 3/2013 |
| WO | 2013055434 A1 | 4/2013 |
| WO | 2013082397 A1 | 6/2013 |
| WO | 2013103291 A2 | 7/2013 |
| WO | 2013131109 A1 | 9/2013 |
| WO | 2013167478 A1 | 11/2013 |
| WO | 2013177716 A1 | 12/2013 |
| WO | 2014041534 A1 | 3/2014 |
| WO | 2014046420 A1 | 3/2014 |
| WO | 2014118518 A1 | 8/2014 |
| WO | 2014160852 A1 | 10/2014 |
| WO | 2015023599 A1 | 2/2015 |
| WO | 2015052348 A1 | 4/2015 |
| WO | 2015068384 A1 | 5/2015 |
| WO | 2015169403 A1 | 11/2015 |
| WO | 2015170307 A1 | 11/2015 |
| WO | 2015197462 A1 | 12/2015 |
| WO | 2016051385 A1 | 4/2016 |
| WO | 2016055989 A1 | 4/2016 |
| WO | 2016071894 A1 | 5/2016 |
| WO | 2016103242 A1 | 6/2016 |
| WO | 2016116915 A1 | 7/2016 |
| WO | 2016124203 A1 | 8/2016 |
| WO | 2016139448 A1 | 9/2016 |

(56) References Cited

FOREIGN PATENT DOCUMENTS

| | | |
|---|---|---|
| WO | 2016166562 A1 | 10/2016 |
| WO | 2016167535 A1 | 10/2016 |
| WO | 2016191574 A1 | 12/2016 |
| WO | 2016200088 A1 | 12/2016 |
| WO | 2016200361 A1 | 12/2016 |
| WO | 2016204731 A1 | 12/2016 |
| WO | 2017001846 A1 | 1/2017 |
| WO | 2017075226 A1 | 5/2017 |
| WO | 2017152198 A1 | 9/2017 |
| WO | 2017153357 A1 | 9/2017 |
| WO | 2017162559 A1 | 9/2017 |
| WO | 2017205446 A1 | 11/2017 |
| WO | 2017209779 A1 | 12/2017 |
| WO | 2017210524 A1 | 12/2017 |
| WO | 2018022414 A1 | 2/2018 |
| WO | 2018044781 A1 | 3/2018 |
| WO | 2018056953 A1 | 3/2018 |
| WO | 2018090550 A1 | 5/2018 |
| WO | 2018138513 A1 | 8/2018 |
| WO | 2018144318 A1 | 8/2018 |
| WO | 2018144463 A1 | 8/2018 |
| WO | 2018150263 A1 | 8/2018 |
| WO | 2018150268 A1 | 8/2018 |
| WO | 2018152156 A1 | 8/2018 |
| WO | 2018183791 A1 | 10/2018 |
| WO | 2018150267 A3 | 11/2018 |
| WO | 2018235026 A1 | 12/2018 |
| WO | 2018235065 A1 | 12/2018 |
| WO | 2019004404 A1 | 1/2019 |
| WO | 2019065541 A1 | 4/2019 |
| WO | 2019096845 A1 | 5/2019 |
| WO | 2019150385 A1 | 8/2019 |
| WO | 2019161094 A1 | 8/2019 |
| WO | 2019188566 A1 | 10/2019 |
| WO | 2019190593 A1 | 10/2019 |
| WO | 2019212949 A1 | 11/2019 |
| WO | 2019212950 A1 | 11/2019 |
| WO | 2019212951 A1 | 11/2019 |
| WO | 2019212952 A1 | 11/2019 |
| WO | 2019212954 A1 | 11/2019 |
| WO | 2019212955 A1 | 11/2019 |
| WO | 2019212956 A1 | 11/2019 |
| WO | 2019214787 A1 | 11/2019 |
| WO | 2019214788 A1 | 11/2019 |
| WO | 2020000994 A1 | 1/2020 |
| WO | 2020020618 A1 | 1/2020 |
| WO | 2020038822 A1 | 2/2020 |
| WO | 2020088409 A1 | 5/2020 |
| WO | 2020049394 A3 | 6/2020 |
| WO | 2020120657 A1 | 6/2020 |
| WO | 2020152575 A1 | 7/2020 |
| WO | 2020182923 A1 | 9/2020 |
| WO | 2020204967 A1 | 10/2020 |
| WO | 2020209898 A1 | 10/2020 |
| WO | 2020242790 A1 | 12/2020 |
| WO | 2020251893 A1 | 12/2020 |
| WO | 2020256865 A1 | 12/2020 |
| WO | 2021007144 A1 | 1/2021 |
| WO | 2021007345 A1 | 1/2021 |
| WO | 2021010844 A1 | 1/2021 |
| WO | 2021016026 A1 | 1/2021 |
| WO | 2021016300 A1 | 1/2021 |
| WO | 2021025919 A1 | 2/2021 |
| WO | 2021034886 A1 | 2/2021 |
| WO | 2021041123 A1 | 3/2021 |
| WO | 2021086868 A1 | 5/2021 |
| WO | 2021094352 A1 | 5/2021 |
| WO | 2021102296 A1 | 5/2021 |
| WO | WO-2021094639 A1 * | 5/2021 ........... A61B 10/007 |
| WO | 2021138411 A1 | 7/2021 |
| WO | 2021138414 A1 | 7/2021 |
| WO | 2021155206 A1 | 8/2021 |
| WO | 2021173436 A1 | 9/2021 |
| WO | 2021195384 A1 | 9/2021 |
| WO | 2021207621 A1 | 10/2021 |
| WO | 2021211568 A1 | 10/2021 |
| WO | 2021216419 A1 | 10/2021 |
| WO | 2021216422 A1 | 10/2021 |
| WO | 2021231532 A1 | 11/2021 |
| WO | 2021247523 A1 | 12/2021 |
| WO | 2021257202 A1 | 12/2021 |
| WO | 2022006256 A1 | 1/2022 |
| WO | 2022031943 A1 | 2/2022 |
| WO | 2022035745 A1 | 2/2022 |
| WO | 2022076427 A2 | 4/2022 |
| WO | 2022086898 A1 | 4/2022 |
| WO | 2022098536 A1 | 5/2022 |
| WO | 2022125685 A1 | 6/2022 |
| WO | 2022140545 A1 | 6/2022 |
| WO | 2022150360 A1 | 7/2022 |
| WO | 2022150463 A1 | 7/2022 |
| WO | 2022159392 A1 | 7/2022 |
| WO | 2022170182 A1 | 8/2022 |
| WO | 2022182385 A1 | 9/2022 |
| WO | 2022192188 A1 | 9/2022 |
| WO | 2022192347 A1 | 9/2022 |
| WO | 2023014641 A1 | 2/2023 |
| WO | 2023034453 A1 | 3/2023 |
| WO | 2023038945 A1 | 3/2023 |
| WO | 2023038950 A1 | 3/2023 |
| WO | 2023049175 A1 | 3/2023 |
| WO | WO-2023086394 A1 * | 5/2023 |
| WO | 2023191764 A1 | 10/2023 |

OTHER PUBLICATIONS

Advisory Action for U.S. Appl. No. 14/722,613 mailed Mar. 4, 2019.
Advisory Action for U.S. Appl. No. 14/952,591 mailed Jun. 1, 2018.
Advisory Action for U.S. Appl. No. 15/238,427 mailed Apr. 10, 2019.
Action for U.S. Appl. No. 16/899,956 mailed Jul. 9, 2021.
Advisory Action for U.S. Appl. No. 16/904,868 mailed Jul. 2, 2021.
Advisory Action for U.S. Appl. No. 16/905,400 mailed Feb. 16, 2022.
Advisory Action for U.S. Appl. No. 16/905,400 mailed Jun. 9, 2021.
Corrected International Search Report and Written Opinion for International Application No. PCT/US2017/043025 mailed Jan. 11, 2018.
Corrected Notice of Allowability for U.S. Appl. No. 15/221,106 mailed Jul. 2, 2019.
Corrected Notice of Allowability for U.S. Appl. No. 15/612,325 mailed Mar. 17, 2021.
Corrected Notice of Allowability for U.S. Appl. No. 17/330,657 mailed Dec. 9, 2021.
Final Office Action for U.S. Appl. No. 14/722,613 mailed on Nov. 29, 2018.
Final Office Action for U.S. Appl. No. 14/947,759 mailed Apr. 8, 2016.
Final Office Action for U.S. Appl. No. 14/952,591 mailed Feb. 23, 2018.
Final Office Action for U.S. Appl. No. 14/952,591 mailed Nov. 1, 2019.
Final Office Action for U.S. Appl. No. 14/952,591 mailed Nov. 27, 2020.
Final Office Action for U.S. Appl. No. 15/171,968 mailed Feb. 14, 2020.
Final Office Action for U.S. Appl. No. 15/171,968 mailed Mar. 19, 2019.
Final Office Action for U.S. Appl. No. 15/221,106 mailed Jan. 23, 2019.
Final Office Action for U.S. Appl. No. 15/238,427 mailed Jan. 2, 2019.
Final Office Action for U.S. Appl. No. 15/260,103 mailed Feb. 14, 2019.
Final Office Action for U.S. Appl. No. 15/612,325 mailed Sep. 17, 2020.
Final Office Action for U.S. Appl. No. 16/452,145 mailed Mar. 25, 2022.

(56) References Cited

OTHER PUBLICATIONS

Final Office Action for U.S. Appl. No. 16/899,956 mailed Apr. 19, 2021.
Final Office Action for U.S. Appl. No. 16/904,868 mailed Mar. 10, 2022.
Final Office Action for U.S. Appl. No. 16/904,868 mailed Mar. 26, 2021.
Final Office Action for U.S. Appl. No. 16/905,400 mailed Apr. 6, 2021.
Final Office Action for U.S. Appl. No. 16/905,400 mailed Dec. 9, 2021.
Final Office Action for U.S. Appl. No. 17/088,272 mailed May 25, 2021.
Final Office Action for U.S. Appl. No. 29/624,661 mailed Feb. 18, 2020.
International Search Report and Written Opinion from International Application No. PCT/US2016/049274 mailed Dec. 1, 2016.
International Search Report and Written Opinion from International Application No. PCT/US2017/035625 mailed Aug. 15, 2017.
International Search Report and Written Opinion from International Application No. PCT/US2017/043025 mailed Oct. 18, 2017.
International Search Report and Written Opinion from International Application No. PCT/US2018/015968 mailed Apr. 6, 2018.
International Search Report and Written Opinion from International Application No. PCT/US2019/029608 mailed Sep. 3, 2019.
International Search Report and Written Opinion from International Application No. PCT/US2019/029609 mailed Sep. 3, 2019.
International Search Report and Written Opinion from International Application No. PCT/US2019/029610 mailed Sep. 3, 2019.
International Search Report and Written Opinion from International Application No. PCT/US2019/029611 mailed Jul. 3, 2019.
International Search Report and Written Opinion from International Application No. PCT/US2019/029613 mailed Jul. 3, 2019.
International Search Report and Written Opinion from International Application No. PCT/US2019/029614 mailed Sep. 26, 2019.
International Search Report and Written Opinion from International Application No. PCT/US2019/029616 mailed Aug. 30, 2019.
International Search Report and Written Opinion from International Application No. PCT/US2020/023572 mailed Jul. 6, 2020.
International Search Report and Written Opinion from International Application No. PCT/US2020/033064 mailed Aug. 31, 2020.
International Search Report and Written Opinion from International Application No. PCT/US2020/033122 mailed Aug. 31, 2020.
International Search Report and Written Opinion from International Application No. PCT/US2020/040860 mailed Oct. 2, 2020.
International Search Report and Written Opinion from International Application No. PCT/US2020/041242 mailed Nov. 17, 2020.
International Search Report and Written Opinion from International Application No. PCT/US2020/041249 mailed Oct. 2, 2020.
International Search Report and Written Opinion from International Application No. PCT/US2020/042262 mailed Oct. 14, 2020.
International Search Report and Written Opinion from International Application No. PCT/US2020/043059 mailed Oct. 6, 2020.
International Search Report and Written Opinion from International Application No. PCT/US2020/044024 mailed Nov. 12, 2020.
International Search Report and Written Opinion from International Application No. PCT/US2020/046914 mailed Dec. 1, 2020.
International Search Report and Written Opinion from International Application No. PCT/US2020/055680 mailed Dec. 15, 2020.
International Search Report and Written Opinion from International Application No. PCT/US2020/061563 mailed Feb. 19, 2021.
International Search Report and Written Opinion from International Application No. PCT/US2020/065234 mailed Apr. 12, 2021.
International Search Report and Written Opinion from International Application No. PCT/US2020/067451 mailed Mar. 25, 2021.
International Search Report and Written Opinion from International Application No. PCT/US2020/067454 mailed Mar. 29, 2021.
International Search Report and Written Opinion from International Application No. PCT/US2020/067455 mailed Mar. 26, 2021.
International Search Report and Written Opinion from International Application No. PCT/US2021/015024 mailed May 18, 2021.
International Search Report and Written Opinion from International Application No. PCT/US2021/015787 mailed May 27, 2021.
International Search Report and Written Opinion from International Application No. PCT/US2021/023001 mailed Jun. 21, 2021.
International Search Report and Written Opinion from International Application No. PCT/US2021/024162 mailed Jul. 8, 2021.
International Search Report and Written Opinion from International Application No. PCT/US2021/027061 mailed Jul. 19, 2021.
International Search Report and Written Opinion from International Application No. PCT/US2021/027104 mailed Jul. 6, 2021.
International Search Report and Written Opinion from International Application No. PCT/US2021/027314 mailed Jul. 6, 2021.
International Search Report and Written Opinion from International Application No. PCT/US2021/027422 mailed Aug. 12, 2021.
International Search Report and Written Opinion from International Application No. PCT/US2021/027425 mailed Aug. 11, 2021.
International Search Report and Written Opinion from International Application No. PCT/US2021/027913 mailed Jul. 12, 2021.
International Search Report and Written Opinion from International Application No. PCT/US2021/027917 mailed Aug. 19, 2021.
International Search Report and Written Opinion from International Application No. PCT/US2021/035181 mailed Sep. 16, 2021.
International Search Report and Written Opinion from International Application No. PCT/US2021/043893 mailed Nov. 22, 2021.
International Search Report and Written Opinion from International Application No. PCT/US2021/044699 mailed Nov. 22, 2021.
International Search Report and Written Opinion from International Application No. PCT/US2021/045188 mailed Jan. 26, 2022.
International Search Report and Written Opinion from International Application No. PCT/US2021/047536 mailed Dec. 23, 2021.
International Search Report and Written Opinion from International Application No. PCT/US2021/048211 mailed Dec. 22, 2021.
International Search Report and Written Opinion from International Application No. PCT/US2021/048661 mailed Feb. 14, 2022.
International Search Report and Written Opinion from International Application No. PCT/US2021/056566 mailed Feb. 11, 2022.
Issue Notification for U.S. Appl. No. 14/952,591 mailed Jul. 28, 2021.
Issue Notification for U.S. Appl. No. 15/171,968 mailed Mar. 3, 2021.
Issue Notification for U.S. Appl. No. 15/221,106 mailed Jul. 24, 2019.
Issue Notification for U.S. Appl. No. 15/238,427 mailed Jul. 24, 2019.
Issue Notification for U.S. Appl. No. 15/260,103 mailed Aug. 7, 2019.
Issue Notification for U.S. Appl. No. 15/611,587 mailed Feb. 20, 2019.
Issue Notification for U.S. Appl. No. 15/612,325 mailed Mar. 24, 2021.
Issue Notification for U.S. Appl. No. 29/624,661 mailed Aug. 4, 2021.
Non-Final Office Action for U.S. Appl. No. 14/592,591 mailed Mar. 20, 2020.
Non-Final Office Action for U.S. Appl. No. 14/722,613 mailed Jun. 13, 2019.
Non-Final Office Action for U.S. Appl. No. 14/947,759 mailed Mar. 17, 2016.
Non-Final Office Action for U.S. Appl. No. 14/952,591 mailed Aug. 1, 2017.
Non-Final Office Action for U.S. Appl. No. 14/952,591 mailed Mar. 20, 2020.
Non-Final Office Action for U.S. Appl. No. 14/952,591 mailed Mar. 21, 2019.
Non-Final Office Action for U.S. Appl. No. 14/952,591 mailed Sep. 28, 2018.
Non-Final Office Action for U.S. Appl. No. 15/171,968 mailed May 11, 2020.
Non-Final Office Action for U.S. Appl. No. 15/171,968 mailed Aug. 20, 2019.

(56) References Cited

OTHER PUBLICATIONS

Non-Final Office Action for U.S. Appl. No. 15/171,968 mailed Jun. 12, 2018.
Non-Final Office Action for U.S. Appl. No. 15/221,106 mailed Jun. 5, 2018.
Non-Final Office Action for U.S. Appl. No. 15/238,427 mailed Aug. 8, 2018.
Non-Final Office Action for U.S. Appl. No. 15/260,103 mailed Sep. 26, 2018.
Non-Final Office Action for U.S. Appl. No. 15/611,587 mailed Dec. 29, 2017.
Non-Final Office Action for U.S. Appl. No. 15/611,587 mailed Jul. 13, 2018.
Non-Final Office Action for U.S. Appl. No. 15/612,325 mailed Mar. 19, 2020.
Non-Final Office Action for U.S. Appl. No. 16/245,726 mailed Jan. 21, 2022.
Non-Final Office Action for U.S. Appl. No. 16/449,039 mailed Dec. 8, 2021.
Non-Final Office Action for U.S. Appl. No. 16/452,145 mailed Sep. 28, 2021.
Non-Final Office Action for U.S. Appl. No. 16/452,258 mailed Sep. 28, 2021.
Non-Final Office Action for U.S. Appl. No. 16/478,180 mailed Oct. 22, 2021.
Non-Final Office Action for U.S. Appl. No. 16/899,956 mailed Oct. 16, 2020.
Non-Final Office Action for U.S. Appl. No. 16/899,956 mailed Sep. 2, 2021.
Non-Final Office Action for U.S. Appl. No. 16/904,868 mailed Nov. 25, 2020.
Non-Final Office Action for U.S. Appl. No. 16/904,868 mailed Oct. 5, 2021.
Non-Final Office Action for U.S. Appl. No. 16/905,400 mailed Dec. 2, 2020.
Non-Final Office Action for U.S. Appl. No. 16/905,400 mailed Jul. 22, 2021.
Non-Final Office Action for U.S. Appl. No. 17/088,272 mailed Jan. 25, 2021.
Non-Final Office Action for U.S. Appl. No. 17/330,657 mailed Aug. 11, 2021.
Non-Final Office Action for U.S. Appl. No. 29/624,661 mailed Jul. 18, 2019.
Non-Final Office Action for U.S. Appl. No. 29/694,002 mailed Jun. 24, 2020.
Non-Final Office Action for U.S. Appl. No. 29/741,751 mailed Jan. 18, 2022.
Notice of Allowance for U.S. Appl. No. 14/952,591 mailed Apr. 5, 2021.
Notice of Allowance for U.S. Appl. No. 14/952,591 mailed Jul. 8, 2021.
Notice of Allowance for U.S. Appl. No. 15/171,968 mailed Feb. 16, 2021.
Notice of Allowance for U.S. Appl. No. 15/171,968 mailed Nov. 6, 2020.
Notice of Allowance for U.S. Appl. No. 15/221,106 mailed May 1, 2019.
Notice of Allowance for U.S. Appl. No. 15/238,427 mailed May 23, 2019.
Notice of Allowance for U.S. Appl. No. 15/260,103 mailed Jun. 7, 2019.
Notice of Allowance for U.S. Appl. No. 15/611,587 mailed Dec. 21, 2018.
Notice of Allowance for U.S. Appl. No. 15/612,325 mailed Feb. 19, 2021.
Notice of Allowance for U.S. Appl. No. 15/612,325 mailed Jan. 21, 2021.
Notice of Allowance for U.S. Appl. No. 16/899,956 mailed Dec. 29, 2021.
Notice of Allowance for U.S. Appl. No. 17/088,272 mailed Aug. 5, 2021.
Notice of Allowance for U.S. Appl. No. 17/088,272 mailed Mar. 4, 2022.
Notice of Allowance for U.S. Appl. No. 17/088,272 mailed Nov. 24, 2021.
Notice of Allowance for U.S. Appl. No. 17/330,657 mailed Mar. 16, 2022.
Notice of Allowance for U.S. Appl. No. 17/330,657 mailed Nov. 26, 2021.
Notice of Allowance for U.S. Appl. No. 29/624,661 mailed Apr. 28, 2021.
Notice of Allowance for U.S. Appl. No. 29/624,661 mailed Jul. 10, 2020.
Notice of Allowance for U.S. Appl. No. 29/624,661 mailed May 14, 2020.
Notice of Allowance for U.S. Appl. No. 29/624,661 mailed Sep. 29, 2020.
Notice of Allowance for U.S. Appl. No. 29/694,002 mailed Apr. 29, 2021.
Notice of Allowance for U.S. Appl. No. 29/694,002 mailed Jan. 29, 2021.
Notice of Allowance for U.S. Appl. No. 29/694,002 mailed Oct. 16, 2020.
Notice to File Missing Parts for U.S. Appl. No. 17/179,116 mailed Mar. 3, 2021.
Restriction Requirement for U.S. Appl. No. 16/433,773 mailed Dec. 7, 2021.
Restriction Requirement for U.S. Appl. No. 16/478,180 mailed May 25, 2021.
U.S. Appl. No. 14/625,469, filed Feb. 28, 2015.
U.S. Appl. No. 14/947,759, filed Nov. 20, 2015.
U.S. Appl. No. 14/952,591, filed Nov. 25, 2015.
U.S. Appl. No. 15/171,968, filed Jun. 2, 2016.
U.S. Appl. No. 15/221,106, filed Jul. 27, 2016.
U.S. Appl. No. 15/384,196 filed Dec. 19, 2016.
U.S. Appl. No. 16/245,726, filed Jan. 11, 2019.
U.S. Appl. No. 16/369,676, filed Mar. 29, 2019.
U.S. Appl. No. 16/433,773, filed Jun. 6, 2019.
U.S. Appl. No. 16/449,039, filed Jun. 21, 2019.
U.S. Appl. No. 16/452,145, filed Jun. 25, 2019.
U.S. Appl. No. 16/452,258, filed Jun. 25, 2019.
U.S. Appl. No. 16/478,180, filed Jul. 16, 2019.
U.S. Appl. No. 16/904,868, filed Jun. 18, 2020.
U.S. Appl. No. 16/905,400, filed Jun. 18, 2020.
U.S. Appl. No. 17/051,550, filed Oct. 29, 2020.
U.S. Appl. No. 17/051,554, filed Oct. 29, 2020.
U.S. Appl. No. 17/051,585, filed Oct. 29, 2020.
U.S. Appl. No. 17/051,600, filed Oct. 29, 2020.
U.S. Appl. No. 17/088,272, filed Nov. 3, 2020.
U.S. Appl. No. 17/179,116, filed Feb. 18, 2021.
U.S. Appl. No. 17/330,657, filed May 26, 2021.
U.S. Appl. No. 17/378,015, filed Jul. 16, 2021.
U.S. Appl. No. 17/394,055, filed Aug. 4, 2021.
U.S. Appl. No. 17/412,864, filed Aug. 26, 2021.
U.S. Appl. No. 17/444,825, filed Aug. 10, 2021.
U.S. Appl. No. 17/446,256, filed Aug. 27, 2021.
U.S. Appl. No. 17/446,654, filed Sep. 1, 2021.
U.S. Appl. No. 17/447,123, filed Sep. 8, 2021.
U.S. Appl. No. 17/450,864, filed Oct. 14, 2021.
U.S. Appl. No. 17/451,345, filed Oct. 19, 2021.
U.S. Appl. No. 17/451,354, filed Oct. 19, 2021.
U.S. Appl. No. 17/453,260, filed Nov. 2, 2021.
U.S. Appl. No. 17/461,036 mailed Aug. 30, 2021.
U.S. Appl. No. 17/494,578, filed Oct. 5, 2021.
U.S. Appl. No. 17/501,591, filed Oct. 14, 2021.
U.S. Appl. No. 17/595,747, filed Nov. 23, 2021.
U.S. Appl. No. 17/597,408, filed Jan. 5, 2022.
U.S. Appl. No. 17/597,673, filed Jan. 18, 2022.
U.S. Appl. No. 17/614,173, filed Nov. 24, 2021.
U.S. Appl. No. 17/631,619, filed Jan. 31, 2022.
U.S. Appl. No. 17/645,821, filed Dec. 23, 2021.
U.S. Appl. No. 17/646,771, filed Jan. 3, 2022.

(56) References Cited

OTHER PUBLICATIONS

U.S. Appl. No. 17/653,314, filed Mar. 3, 2022.
U.S. Appl. No. 17/653,920, filed Mar. 8, 2022.
U.S. Appl. No. 17/654,156, filed Mar. 9, 2022.
U.S. Appl. No. 17/655,464, filed Mar. 18, 2022.
U.S. Appl. No. 29/741,751, filed Jul. 15, 2020.
U.S. Appl. No. 61/955,537, filed Mar. 19, 2014.
U.S. Appl. No. 62/082,279, filed Nov. 20, 2014.
U.S. Appl. No. 62/084,078, filed Nov. 25, 2014.
U.S. Appl. No. 62/414,963, filed Oct. 31, 2016.
U.S. Appl. No. 62/452,437, filed Jan. 31, 2017.
U.S. Appl. No. 62/485,578, filed Apr. 14, 2017.
U.S. Appl. No. 62/665,297, filed May 1, 2018.
U.S. Appl. No. 62/665,302, filed May 1, 2018.
U.S. Appl. No. 62/665,317, filed May 1, 2018.
U.S. Appl. No. 62/665,321, filed May 1, 2018.
U.S. Appl. No. 62/665,331, filed May 1, 2018.
U.S. Appl. No. 62/665,335, filed May 1, 2018.
U.S. Appl. No. 62/853,279, filed May 28, 2019.
U.S. Appl. No. 62/853,889, filed May 29, 2019.
U.S. Appl. No. 62/864,656, filed Jun. 21, 2019.
U.S. Appl. No. 62/873,045, filed Jul. 11, 2019.
U.S. Appl. No. 62/873,048, filed Jul. 11, 2019.
U.S. Appl. No. 62/876,500, filed Jul. 19, 2019.
U.S. Appl. No. 62/877,558, filed Jul. 23, 2019.
U.S. Appl. No. 62/883,172, filed Aug. 6, 2019.
U.S. Appl. No. 62/889,149, filed Aug. 20, 2019.
U.S. Appl. No. 62/935,337, filed Nov. 14, 2019.
U.S. Appl. No. 62/938,447, filed Nov. 21, 2019.
U.S. Appl. No. 62/949,187, filed Dec. 17, 2019.
U.S. Appl. No. 62/956,756, filed Jan. 3, 2020.
U.S. Appl. No. 62/956,767, filed Jan. 3, 2020.
U.S. Appl. No. 62/956,770, filed Jan. 3, 2020.
U.S. Appl. No. 62/967,977, filed Jan. 30, 2020.
U.S. Appl. No. 62/994,912, filed Mar. 26, 2020.
U.S. Appl. No. 63/011,445, filed Apr. 17, 2020.
U.S. Appl. No. 63/011,487, filed Apr. 17, 2020.
U.S. Appl. No. 63/011,571, filed Apr. 17, 2020.
U.S. Appl. No. 63/011,657, filed Apr. 17, 2020.
U.S. Appl. No. 63/011,760, filed Apr. 17, 2020.
U.S. Appl. No. 63/012,347, filed Apr. 20, 2020.
U.S. Appl. No. 63/012,384, filed Apr. 20, 2020.
U.S. Appl. No. 63/030,685, filed May 27, 2020.
U.S. Appl. No. 63/033,310, filed Jun. 2, 2020.
U.S. Appl. No. 63/047,374, filed Jul. 2, 2020.
U.S. Appl. No. 63/061,241, filed Aug. 5, 2020.
U.S. Appl. No. 63/061,244, filed Aug. 5, 2020.
U.S. Appl. No. 63/061,834, filed Aug. 6, 2020.
U.S. Appl. No. 63/064,017, filed Aug. 11, 2020.
U.S. Appl. No. 63/064,126, filed Aug. 11, 2020.
U.S. Appl. No. 63/067,542, filed Aug. 19, 2020.
U.S. Appl. No. 63/071,438, filed Aug. 28, 2020.
U.S. Appl. No. 63/071,821, filed Aug. 28, 2020.
U.S. Appl. No. 63/073,545, filed Sep. 2, 2020.
U.S. Appl. No. 63/073,553, filed Sep. 2, 2020.
U.S. Appl. No. 63/074,051, filed Sep. 3, 2020.
U.S. Appl. No. 63/074,066, filed Sep. 3, 2020.
U.S. Appl. No. 63/076,032, filed Sep. 9, 2020.
U.S. Appl. No. 63/076,474, filed Sep. 10, 2020.
U.S. Appl. No. 63/076,477, filed Sep. 10, 2020.
U.S. Appl. No. 63/082,261, filed Sep. 23, 2020.
U.S. Appl. No. 63/088,506, filed Oct. 7, 2020.
U.S. Appl. No. 63/088,511, filed Oct. 7, 2020.
U.S. Appl. No. 63/088,539, filed Oct. 7, 2020.
U.S. Appl. No. 63/094,464, filed Oct. 21, 2020.
U.S. Appl. No. 63/094,498, filed Oct. 21, 2020.
U.S. Appl. No. 63/094,594, filed Oct. 21, 2020.
U.S. Appl. No. 63/094,608, filed Oct. 21, 2020.
U.S. Appl. No. 63/094,626, filed Oct. 21, 2020.
U.S. Appl. No. 63/109,066, filed Nov. 3, 2020.
U.S. Appl. No. 63/109,084, filed Nov. 3, 2020.
U.S. Appl. No. 63/112,417, filed Nov. 11, 2020.
U.S. Appl. No. 63/119,161, filed Nov. 30, 2020.
U.S. Appl. No. 63/124,271, filed Dec. 11, 2020.
U.S. Appl. No. 63/133,892, filed Jan. 5, 2021.
U.S. Appl. No. 63/134,287, filed Jan. 6, 2021.
U.S. Appl. No. 63/134,450, filed Jan. 6, 2021.
U.S. Appl. No. 63/134,631, filed Jan. 7, 2021.
U.S. Appl. No. 63/134,632, filed Jan. 7, 2021.
U.S. Appl. No. 63/134,754, filed Jan. 7, 2021.
U.S. Appl. No. 63/138,878, filed Jan. 19, 2021.
U.S. Appl. No. 63/146,946, filed Feb. 8, 2021.
U.S. Appl. No. 63/147,013, filed Feb. 8, 2021.
U.S. Appl. No. 63/147,299, filed Feb. 9, 2021.
U.S. Appl. No. 63/148,723, filed Feb. 12, 2021.
U.S. Appl. No. 63/154,248, filed Feb. 26, 2021.
U.S. Appl. No. 63/155,395, filed Mar. 2, 2021.
U.S. Appl. No. 63/157,007, filed Mar. 5, 2021.
U.S. Appl. No. 63/157,014, filed Mar. 5, 2021.
U.S. Appl. No. 63/159,142, filed Mar. 10, 2021.
U.S. Appl. No. 63/159,186, filed Mar. 10, 2021.
U.S. Appl. No. 63/159,210, filed Mar. 10, 2021.
U.S. Appl. No. 63/159,280, filed Mar. 10, 2021.
U.S. Appl. No. 63/165,273, filed Mar. 24, 2021.
U.S. Appl. No. 63/165,384, filed Mar. 24, 2021.
U.S. Appl. No. 63/171,165, filed Apr. 6, 2021.
U.S. Appl. No. 63/172,975, filed Apr. 9, 2021.
U.S. Appl. No. 63/181,695, filed Apr. 29, 2021.
U.S. Appl. No. 63/192,274, filed May 24, 2021.
U.S. Appl. No. 63/193,235, filed May 26, 2021.
U.S. Appl. No. 63/193,406, filed May 26, 2021.
U.S. Appl. No. 63/193,891, filed May 27, 2021.
U.S. Appl. No. 63/208,262, filed Jun. 8, 2021.
U.S. Appl. No. 63/214,551, filed Jun. 24, 2021.
U.S. Appl. No. 63/214,570, filed Jun. 24, 2021.
U.S. Appl. No. 63/215,017, filed Jun. 25, 2021.
U.S. Appl. No. 63/228,244, filed Aug. 2, 2021.
U.S. Appl. No. 63/228,252, filed Aug. 2, 2021.
U.S. Appl. No. 63/228,258, filed Aug. 2, 2021.
U.S. Appl. No. 63/230,894, filed Aug. 9, 2021.
U.S. Appl. No. 63/238,457, filed Aug. 30, 2021.
U.S. Appl. No. 63/238,477, filed Aug. 30, 2021.
U.S. Appl. No. 63/241,562, filed Sep. 8, 2021.
U.S. Appl. No. 63/241,564, filed Sep. 8, 2021.
U.S. Appl. No. 63/241,575, filed Sep. 8, 2021.
U.S. Appl. No. 63/246,972, filed Sep. 22, 2021.
U.S. Appl. No. 63/247,375, filed Sep. 23, 2021.
U.S. Appl. No. 63/247,478, filed Sep. 23, 2021.
U.S. Appl. No. 63/247,491, filed Sep. 23, 2021.
U.S. Appl. No. 63/299,208, filed Jan. 13, 2022.
Sage's Second Supplemental Invalidity Contentions Regarding U.S. Pat. No. 8,287,508, U.S. Pat. No. 10,226,375, U.S. Pat. No. 10,390,989, and U.S. Pat. No. 10,376,407, 292 pages.
Plaintiff's Identification of Claim Terms and Proposed Constructions, 3 pages.
Sage's Preliminary Identification of Claim Elements and Proposed Constructions for U.S. Pat. No. 8,287,508, U.S. Pat. No. 10,226,376, U.S. Pat. No. 10,390,989 and U.S. Pat. No. 10,376,407, 7 pages.
Corrected Certificate of Service, 2020, 2 pages.
Excerpts from the 508 (U.S. Pat. No. 8,278,508) Patent's Prosecution History, 2020, 99 pages.
Declaration of Diane K. Newman Curriculum Vitae, 2020, pp. 1-199.
Sage's Supplemental and Initial Invalidity Contentions Regarding U.S. Pat. No. 8,287,508; U.S. Pat. No. 10,226,375; U.S. Pat. No. 10,390,989 and Initial Invalidity Contentions Regarding U.S. Pat. No. 10,376,407, Aug. 21, 2020, 277 pages.
Decision Granting Institution of Inter Partes Review for U.S. Pat. No. 8,287,508, Feb. 17, 2021, 39 pages.
Memorandum Order, Feb. 2021, 14 pgs.
Boehringer CareDry System—Second Generation for Non-Invasive Urinary Management for Females, Mar. 2021, 3 pgs.

(56) References Cited

OTHER PUBLICATIONS

PureWick's Response to Interrogatory No. 9 in *PureWick, LLC v. Sage Products, LLC*, Mar. 23, 2020, 6 pages.
Sage's Initial Invalidity Contentions Regarding U.S. Pat. No. 8,287,508; U.S. Pat. No. 10,226,375; and U.S. Pat. No. 10,390,989, May 29, 2020, 193 pages.
Defendant and Counterclaim Plaintiff Sage Products, LLC's Answer, Defenses, and Counterclaims to Plaintiff's Amended Complaint, Nov. 1, 2019.
Plaintiff's Opening Claim Construction Brief, Oct. 16, 2020, 26 pages.
"3 Devices Take Top Honors in Dare-To-Dream Medtech Design Contest", R+D Digest, Nov. 2013, 1 page.
"Advanced Mission Extender Device (AMDX) Products", Omni Medical Systems, Inc., 15 pages.
"AMXD Control Starter Kit Brochure", https://www.omnimedicalsys.com/index.php?page=products, 8 pages.
"AMXDmax In-Flight Bladder Relief", Omni Medical; Omni Medical Systems, Inc., 2015.
"AMXDX—Advanced Mission Extender Device Brochure", Omni Medical, 2 pages.
"External Urine Management for Female Anatomy", https://www.stryker.com/us/en/sage/products/sage-primafit.html, Jul. 2020, 4 pages.
"High Absorbancy Cellulose Acetate Electrospun Nanofibers for Feminine Hygiene Application", https://www.sciencedirect.com/science/article/abs/pii/S2352940716300701?via%3Dihub, Jul. 2016, 3 pages.
"How Period Panties Work", www.shethinx.com/pages/thinx-itworks, 2020, 10 pages.
"Hydrogel properties of electrospun polyvinylpyrrolidone and polyvinylpyrrolidone/poly(acrylic acid) blend nanofibers", https://pubs.rsc.org/en/content/articlelanding/2015/ra/c5ra07514a#!divAbstract, 2015, 5 pages.
"In Flight Bladder Relief", Omni Medical, 14 pages.
"Making Women's Sanitary Products Safer and Cheaper", https://www.elsevier.com/connect/making-womens-sanitary-products-safer-and-cheaper, Sep. 2016, 10 pages.
"Novel Nanofibers Make Safe and Effective Absorbent for Sanitary Products", https://www.materialstoday.com/nanomaterials/news/nanofibers-make-safe-and-effective-absorbent/, Oct. 2016, 3 pages.
"Research and Development Work Relating to Assistive Technology Jun. 2005", British Department of Health, Nov. 2006, 40 pages.
"Rising Warrior Insulated Gallon Jug Cover", https://www.amazon.com/Rising-Warrior-Insulated-Sleeve, 2021, 2 pages.
"Step by Step How Ur24 WorksHome", http://medicalpatentur24.com, Aug. 30, 2017, 4 pages.
"Underwear that absorbs your period", Thinx!, 7 pages.
"Urine Bag Cover—Catheter Bag Cover 2000 ml Volume—Medline Style—Multiple Sclerosis—Spine Injury—Suprapublic Catheter—Bladder Incontinence", https://www.etsy.com/listing/1142934658/urine-bag-cover-caatheter-bag-cover-2000, 2022, 1 page.
"User & Maintenance Guide", Omni Medical, 2007, 16 pages.
"Vinyl Dust Cover, Janome #741811000, Janome, Sewing Parts Online", https://www.sewingpartsonline.com/vinyl-dust-cover-janome-74181000, 2020, 2 pages.
"Winners Announced for Dare-to-Dream Medtech Design Challenge", https://www.mddionline.com/design-engineering/winners-announced-dare-dream-medtech-design-challenge, 2014, 4 pages.
Ali, "Sustainability Assessment: Seventh Generation Diapers versus gDiapers", The University of Vermont, Dec. 6, 2011, pp. 1-31.
Autumn, et al., "Frictional adhesion: a new angle on gecko attachment", The Journal of Experimental Biology, 2006, pp. 3569-3579.
Cañas, et al., "Effect of nano- and micro-roughness on adhesion of bioinspired micropatterned surfaces", Acta Biomaterialia 8, 2012, pp. 282-288.
Chaudhary, et al., "Bioinspired dry adhesive: Poly(dimethylsiloxane) grafted with poly(2-ethylhexyl acrylate) brushes", European Polymer Journal, 2015, pp. 432-440.
Dai, et al., "Non-sticky and Non-slippery Biomimetic Patterned Surfaces", Journal of Bionic Engineering, Mar. 2020, pp. 326-334.
Espinoza-Ramirez, "Nanobiodiversity and Biomimetic Adhesives Development: From Nature to Production and Application", Journal of Biomaterials and Nanobiotechnology, pp. 78-101, 2019.
Hollister, "Female Urinary and Pouch and Male Urinary Pouch Brochure", 2011, 1 page.
Hollister, "Male Urinary Pouch External Collection Device", http://www.hollister.com/en/products/Continence-Care-Products/Urine-Collectors/Urine-Collection-Accessories/Male-Urinary-Pouch-External-Collection-Device.
Hollister, "Retracted Penis Pouch by Hollister", Vitality Medical.com, 6 pages.
Purewick, "Incontinence Relief for Women", Presentation, Sep. 23, 2015, 7 pages.
Pytlik, "Super Absorbent Polymers", University of Buffalo.
Sachtman, "New Relief for Pilots? It Depends", Wired, 2008, 2 pages.
Tsipenyuk, et al., "Use of biomimetic hexagonal surface texture in friction against lubricated skin", Journal of the Royal Society—Interface, 2014, pp. 1-6.
Advisory Action for U.S. Appl. No. 16/245,726 mailed Apr. 19, 2023.
Advisory Action for U.S. Appl. No. 16/369,676 mailed Mar. 24, 2023.
Advisory Action for U.S. Appl. No. 16/433,773 mailed Dec. 29, 2023.
Advisory Action for U.S. Appl. No. 16/433,773 mailed Feb. 15, 2023.
Advisory Action for U.S. Appl. No. 16/452,258 mailed Oct. 26, 2022.
Advisory Action for U.S. Appl. No. 16/478,180 mailed Sep. 21, 2022.
Advisory Action for U.S. Appl. No. 16/478,180 mailed Sep. 7, 2023.
Advisory Action for U.S. Appl. No. 16/904,868 mailed Jan. 2, 2024.
Advisory Action for U.S. Appl. No. 16/904,868 mailed Jun. 15, 2022.
Advisory Action for U.S. Appl. No. 17/051,550 mailed Sep. 8, 2023.
Advisory Action for U.S. Appl. No. 17/051,585 mailed Oct. 17, 2023.
Advisory Action for U.S. Appl. No. 17/444,792 mailed Aug. 25, 2023.
Advisory Action for U.S. Appl. No. 17/446,256 mailed Dec. 8, 2023.
Advisory Action for U.S. Appl. No. 17/448,811 mailed Nov. 15, 2023.
Advisory Action for U.S. Appl. No. 17/451,345 mailed Oct. 20, 2023.
Advisory Action for U.S. Appl. No. 17/453,260 mailed Dec. 22, 2023.
Advisory Action for U.S. Appl. No. 17/653,137 mailed Dec. 1, 2023.
Advisory Action for U.S. Appl. No. 17/655,464 mailed Dec. 13, 2023.
Advisory Action for U.S. Appl. No. 17/662,700 mailed Jan. 30, 2023.
Corrected Notice of Allowability for U.S. Appl. No. 16/369,676 mailed Dec. 7, 2023.
Final Office Action for U.S. Appl. No. 16/245,726 mailed Nov. 25, 2022.
Final Office Action for U.S. Appl. No. 16/369,676 mailed Aug. 31, 2023.
Final Office Action for U.S. Appl. No. 16/369,676 mailed Dec. 5, 2022.
Final Office Action for U.S. Appl. No. 16/433,773 mailed Oct. 10, 2023.
Final Office Action for U.S. Appl. No. 16/433,773 mailed Oct. 25, 2022.
Final Office Action for U.S. Appl. No. 16/449,039 mailed Aug. 1, 2022.
Final Office Action for U.S. Appl. No. 16/449,039 mailed Nov. 21, 2023.

(56) References Cited

OTHER PUBLICATIONS

Final Office Action for U.S. Appl. No. 16/452,258 mailed Dec. 21, 2023.
Final Office Action for U.S. Appl. No. 16/452,258 mailed Jun. 14, 2022.
Final Office Action for U.S. Appl. No. 16/478,180 mailed Jun. 22, 2022.
Final Office Action for U.S. Appl. No. 16/478,180 mailed May 31, 2023.
Final Office Action for U.S. Appl. No. 16/904,868 mailed Nov. 2, 2023.
Final Office Action for U.S. Appl. No. 17/051,399 mailed Mar. 9, 2023.
Final Office Action for U.S. Appl. No. 17/051,399 mailed Jan. 8, 2024.
Final Office Action for U.S. Appl. No. 17/051,550 mailed May 23, 2023.
Final Office Action for U.S. Appl. No. 17/051,585 mailed Jul. 27, 2023.
Final Office Action for U.S. Appl. No. 17/179,116 mailed Oct. 31, 2023.
Final Office Action for U.S. Appl. No. 17/444,792 mailed Jun. 15, 2023.
Final Office Action for U.S. Appl. No. 17/446,256 mailed Sep. 19, 2023.
Final Office Action for U.S. Appl. No. 17/448,811 mailed Aug. 3, 2023.
Final Office Action for U.S. Appl. No. 17/450,864 mailed Dec. 28, 2023.
Final Office Action for U.S. Appl. No. 17/451,345 mailed May 3, 2023.
Final Office Action for U.S. Appl. No. 17/451,354 mailed Oct. 30, 2023.
Final Office Action for U.S. Appl. No. 17/453,260 mailed Oct. 5, 2023.
Final Office Action for U.S. Appl. No. 17/501,591 mailed Nov. 14, 2023.
Final Office Action for U.S. Appl. No. 17/646,771 mailed Dec. 21, 2023.
Final Office Action for U.S. Appl. No. 17/653,137 mailed Sep. 21, 2023.
Final Office Action for U.S. Appl. No. 17/655,464 mailed Sep. 1, 2023.
Final Office Action for U.S. Appl. No. 17/661,090 mailed Dec. 11, 2023.
Final Office Action for U.S. Appl. No. 17/662,700 mailed Sep. 30, 2022.
Final Office Action for U.S. Appl. No. 17/663,330 mailed Dec. 12, 2023.
Final Office Action for U.S. Appl. No. 17/664,487 mailed Jan. 4, 2024.
Final Office Action for U.S. Appl. No. 18/139,523 mailed Dec. 22, 2023.
Final Office Action for U.S. Appl. No. 18/164,800 mailed Dec. 6, 2023.
International Search Report and Written Opinion from International Application No. PCT/IB2021/057173 mailed Nov. 5, 2021.
International Search Report and Written Opinion from International Application No. PCT/US2020/057562 mailed Jan. 27, 2021.
International Search Report and Written Opinion from International Application No. PCT/US2021/026607 mailed Jul. 29, 2021.
International Search Report and Written Opinion from International Application No. PCT/US2021/039866 mailed Oct. 7, 2021.
International Search Report and Written Opinion from International Application No. PCT/US2021/049404 mailed Jan. 18, 2022.
International Search Report and Written Opinion from International Application No. PCT/US2021/051456 mailed Jan. 19, 2022.
International Search Report and Written Opinion from International Application No. PCT/US2021/053593 mailed Apr. 11, 2022.
International Search Report and Written Opinion from International Application No. PCT/US2021/055515 mailed Jan. 28, 2022.
International Search Report and Written Opinion from International Application No. PCT/US2021/060993 mailed Mar. 18, 2022.
International Search Report and Written Opinion from International Application No. PCT/US2021/062440 mailed Mar. 28, 2022.
International Search Report and Written Opinion from International Application No. PCT/US2022/011108 mailed Apr. 22, 2022.
International Search Report and Written Opinion from International Application No. PCT/US2022/011281 mailed Apr. 25, 2022.
International Search Report and Written Opinion from International Application No. PCT/US2022/011419 mailed Jun. 7, 2022.
International Search Report and Written Opinion from International Application No. PCT/US2022/011421 mailed Jun. 13, 2022.
International Search Report and Written Opinion from International Application No. PCT/US2022/012794 mailed May 3, 2022.
International Search Report and Written Opinion from International Application No. PCT/US2022/014285 mailed Sep. 28, 2022.
International Search Report and Written Opinion from International Application No. PCT/US2022/014749 mailed Sep. 28, 2022.
International Search Report and Written Opinion from International Application No. PCT/US2022/015026 mailed Oct. 31, 2022.
International Search Report and Written Opinion from International Application No. PCT/US2022/015045 mailed Sep. 9, 2022.
International Search Report and Written Opinion from International Application No. PCT/US2022/015073 mailed Sep. 8, 2022.
International Search Report and Written Opinion from International Application No. PCT/US2022/015418 mailed Nov. 11, 2022.
International Search Report and Written Opinion from International Application No. PCT/US2022/015420 mailed Nov. 18, 2022.
International Search Report and Written Opinion from International Application No. PCT/US2022/015471 mailed May 16, 2022.
International Search Report and Written Opinion from International Application No. PCT/US2022/015492 mailed Apr. 26, 2022.
International Search Report and Written Opinion from International Application No. PCT/US2022/015781 mailed May 6, 2022.
International Search Report and Written Opinion from International Application No. PCT/US2022/016942 mailed Jun. 8, 2022.
International Search Report and Written Opinion from International Application No. PCT/US2022/018159 mailed Dec. 12, 2022.
International Search Report and Written Opinion from International Application No. PCT/US2022/018170 mailed May 31, 2022.
International Search Report and Written Opinion from International Application No. PCT/US2022/019254 mailed Jun. 7, 2022.
International Search Report and Written Opinion from International Application No. PCT/US2022/019480 mailed Jun. 13, 2022.
International Search Report and Written Opinion from International Application No. PCT/US2022/021103 mailed Jun. 23, 2022.
International Search Report and Written Opinion from International Application No. PCT/US2022/022111 mailed Oct. 26, 2022.
International Search Report and Written Opinion from International Application No. PCT/US2022/023594 mailed Jul. 12, 2022.
International Search Report and Written Opinion from International Application No. PCT/US2022/026667 mailed Aug. 22, 2022.
International Search Report and Written Opinion from International Application No. PCT/US2022/030685 mailed Oct. 31, 2022.
International Search Report and Written Opinion from International Application No. PCT/US2022/031032 mailed Sep. 9, 2022.
International Search Report and Written Opinion from International Application No. PCT/US2022/032424 mailed Oct. 11, 2022.
International Search Report and Written Opinion from International Application No. PCT/US2022/034457 mailed Oct. 12, 2022.
International Search Report and Written Opinion from International Application No. PCT/US2022/034744 mailed Dec. 9, 2022.
International Search Report and Written Opinion from International Application No. PCT/US2022/039018 mailed Jan. 10, 2023.
International Search Report and Written Opinion from International Application No. PCT/US2022/039022 mailed Jan. 10, 2023.
International Search Report and Written Opinion from International Application No. PCT/US2022/039711 mailed Jan. 12, 2023.
International Search Report and Written Opinion from International Application No. PCT/US2022/039714 mailed Nov. 22, 2022.

(56) References Cited

OTHER PUBLICATIONS

International Search Report and Written Opinion from International Application No. PCT/US2022/041085 mailed Mar. 16, 2023.
International Search Report and Written Opinion from International Application No. PCT/US2022/041688 mailed Nov. 21, 2022.
International Search Report and Written Opinion from International Application No. PCT/US2022/042719 mailed Dec. 5, 2022.
International Search Report and Written Opinion from International Application No. PCT/US2022/042725 mailed Dec. 19, 2022.
International Search Report and Written Opinion from International Application No. PCT/US2022/043818 mailed Mar. 24, 2023.
International Search Report and Written Opinion from International Application No. PCT/US2022/044107 mailed Dec. 23, 2022.
International Search Report and Written Opinion from International Application No. PCT/US2022/044208 mailed May 8, 2023.
International Search Report and Written Opinion from International Application No. PCT/US2022/044212 mailed Jan. 20, 2023.
International Search Report and Written Opinion from International Application No. PCT/US2022/044243 mailed Feb. 24, 2023.
International Search Report and Written Opinion from International Application No. PCT/US2022/049300 mailed Jun. 6, 2023.
International Search Report and Written Opinion from International Application No. PCT/US2022/050909 mailed Jul. 24, 2023.
International Search Report and Written Opinion from International Application No. PCT/US2023/012696 mailed Jul. 6, 2023.
International Search Report and Written Opinion from International Application No. PCT/US2023/018474 mailed Sep. 11, 2023.
Issue Notification for U.S. Appl. No. 16/245,726 mailed Oct. 18, 2023.
Issue Notification for U.S. Appl. No. 16/899,956 mailed Mar. 29, 2023.
Issue Notification for U.S. Appl. No. 16/905,400 mailed Nov. 30, 2022.
Issue Notification for U.S. Appl. No. 17/088,272 mailed Jun. 15, 2022.
Issue Notification for U.S. Appl. No. 17/330,657 mailed Jun. 22, 2022.
Issue Notification for U.S. Appl. No. 17/461,036 mailed Oct. 11, 2023.
Issue Notification for U.S. Appl. No. 17/663,046 mailed Dec. 20, 2023.
Non-Final Office Action for U.S. Appl. No. 16/369,676 mailed Mar. 31, 2022.
Non-Final Office Action for U.S. Appl. No. 16/433,773 mailed Apr. 11, 2023.
Non-Final Office Action for U.S. Appl. No. 16/433,773 mailed Apr. 21, 2022.
Non-Final Office Action for U.S. Appl. No. 16/449,039 mailed Apr. 27, 2023.
Non-Final Office Action for U.S. Appl. No. 16/452,145 mailed Mar. 28, 2023.
Non-Final Office Action for U.S. Appl. No. 16/452,145 mailed Nov. 2, 2023.
Non-Final Office Action for U.S. Appl. No. 16/452,258 mailed Apr. 26, 2023.
Non-Final Office Action for U.S. Appl. No. 16/478,180 mailed Dec. 20, 2022.
Non-Final Office Action for U.S. Appl. No. 16/478,180 mailed Nov. 7, 2023.
Non-Final Office Action for U.S. Appl. No. 16/904,868 mailed Mar. 15, 2023.
Non-Final Office Action for U.S. Appl. No. 16/905,400 mailed Apr. 27, 2022.
Non-Final Office Action for U.S. Appl. No. 17/051,399 mailed Aug. 18, 2023.
Non-Final Office Action for U.S. Appl. No. 17/051,550 mailed Dec. 15, 2022.
Non-Final Office Action for U.S. Appl. No. 17/051,550 mailed Oct. 24, 2023.
Non-Final Office Action for U.S. Appl. No. 17/051,585 mailed Mar. 29, 2023.
Non-Final Office Action for U.S. Appl. No. 17/051,585 mailed Jan. 8, 2024.
Non-Final Office Action for U.S. Appl. No. 17/179,116 mailed Mar. 24, 2023.
Non-Final Office Action for U.S. Appl. No. 17/326,980 mailed Jul. 11, 2023.
Non-Final Office Action for U.S. Appl. No. 17/444,792 mailed Feb. 10, 2023.
Non-Final Office Action for U.S. Appl. No. 17/444,792 mailed Nov. 17, 2023.
Non-Final Office Action for U.S. Appl. No. 17/446,256 mailed Apr. 13, 2023.
Non-Final Office Action for U.S. Appl. No. 17/446,654 mailed Sep. 8, 2023.
Non-Final Office Action for U.S. Appl. No. 17/448,811 mailed Mar. 1, 2023.
Non-Final Office Action for U.S. Appl. No. 17/450,864 mailed May 10, 2023.
Non-Final Office Action for U.S. Appl. No. 17/451,345 mailed Dec. 7, 2022.
Non-Final Office Action for U.S. Appl. No. 17/451,354 mailed May 3, 2023.
Non-Final Office Action for U.S. Appl. No. 17/453,260 mailed Mar. 14, 2023.
Non-Final Office Action for U.S. Appl. No. 17/501,591 mailed Apr. 25, 2023.
Non-Final Office Action for U.S. Appl. No. 17/645,821 mailed Oct. 25, 2023.
Non-Final Office Action for U.S. Appl. No. 17/646,771 mailed Jul. 5, 2023.
Non-Final Office Action for U.S. Appl. No. 17/653,137 mailed Apr. 7, 2023.
Non-Final Office Action for U.S. Appl. No. 17/655,464 mailed Mar. 14, 2023.
Non-Final Office Action for U.S. Appl. No. 17/657,474 mailed Sep. 12, 2023.
Non-Final Office Action for U.S. Appl. No. 17/661,090 mailed Jul. 6, 2023.
Non-Final Office Action for U.S. Appl. No. 17/662,700 mailed Jul. 22, 2022.
Non-Final Office Action for U.S. Appl. No. 17/663,330 mailed Jun. 29, 2023.
Non-Final Office Action for U.S. Appl. No. 17/664,487 mailed Jun. 8, 2023.
Non-Final Office Action for U.S. Appl. No. 17/808,354 mailed Nov. 28, 2023.
Non-Final Office Action for U.S. Appl. No. 18/139,523 mailed Aug. 17, 2023.
Non-Final Office Action for U.S. Appl. No. 18/140,163 mailed Nov. 9, 2023.
Non-Final Office Action for U.S. Appl. No. 18/140,751 mailed Sep. 14, 2023.
Non-Final Office Action for U.S. Appl. No. 18/198,464 mailed Dec. 7, 2023.
Notice of Allowance for U.S. Appl. No. 16/245,726 mailed Jul. 6, 2023.
Notice of Allowance for U.S. Appl. No. 16/369,676 mailed Nov. 14, 2023.
Notice of Allowance for U.S. Appl. No. 16/449,039 mailed Dec. 15, 2022.
Notice of Allowance for U.S. Appl. No. 16/899,956 mailed Apr. 19, 2022.
Notice of Allowance for U.S. Appl. No. 16/899,956 mailed Aug. 10, 2022.
Notice of Allowance for U.S. Appl. No. 16/899,956 mailed Dec. 1, 2022.
Notice of Allowance for U.S. Appl. No. 16/905,400 mailed Aug. 17, 2022.
Notice of Allowance for U.S. Appl. No. 17/051,554 mailed Jul. 6, 2023.

(56) References Cited

OTHER PUBLICATIONS

Notice of Allowance for U.S. Appl. No. 17/051,554 mailed Oct. 18, 2023.
Notice of Allowance for U.S. Appl. No. 17/461,036 mailed Feb. 22, 2023.
Notice of Allowance for U.S. Appl. No. 17/461,036 mailed Jun. 30, 2023.
Notice of Allowance for U.S. Appl. No. 17/461,036 mailed Oct. 6, 2022.
Notice of Allowance for U.S. Appl. No. 17/662,700 mailed Jul. 28, 2023.
Notice of Allowance for U.S. Appl. No. 17/662,700 mailed Mar. 28, 2023.
Notice of Allowance for U.S. Appl. No. 17/662,700 mailed Nov. 15, 2023.
Notice of Allowance for U.S. Appl. No. 17/663,046 mailed Jan. 30, 2023.
Notice of Allowance for U.S. Appl. No. 18/299,788 mailed Jul. 24, 2023.
Notice of Allowance for U.S. Appl. No. 18/299,788 mailed Nov. 6, 2023.
Notice of Allowance for U.S. Appl. No. 29/741,751 mailed Jun. 9, 2022.
Restriction Requirement for U.S. Appl. No. 17/051,600 mailed Sep. 21, 2023.
Restriction Requirement for U.S. Appl. No. 17/326,980 mailed Mar. 20, 2023.
Restriction Requirement for U.S. Appl. No. 17/446,256 mailed Jan. 23, 2023.
Restriction Requirement for U.S. Appl. No. 17/645,821 mailed Jul. 12, 2023.
Restriction Requirement for U.S. Appl. No. 17/646,771 mailed Apr. 6, 2023.
Restriction Requirement for U.S. Appl. No. 17/657,474 mailed Jun. 30, 2023.
Restriction Requirement for U.S. Appl. No. 18/134,857 mailed Oct. 23, 2023.
Text Messages to Lorena Eckert Re Prototype PureWick Holder dated Apr. 16, 2022.
U.S. Appl. No. 15/260,103, filed Sep. 8, 2016.
U.S. Appl. No. 15/611,587, filed Jun. 1, 2017.
U.S. Appl. No. 15/612,325, filed Jun. 2, 2017.
U.S. Appl. No. 17/451,719, filed Oct. 19, 2021.
U.S. Appl. No. 17/657,474, filed Mar. 31, 2022.
U.S. Appl. No. 17/661,090, filed Apr. 28, 2022.
U.S. Appl. No. 17/662,700, filed May 10, 2022.
U.S. Appl. No. 17/663,046, filed May 12, 2022.
U.S. Appl. No. 17/664,487, filed May 23, 2022.
U.S. Appl. No. 17/664,914, filed May 25, 2022.
U.S. Appl. No. 17/749,340, filed May 20, 2022.
U.S. Appl. No. 17/754,736, filed Apr. 11, 2022.
U.S. Appl. No. 17/756,201, filed May 19, 2022.
U.S. Appl. No. 17/758,152, filed Jun. 29, 2022.
U.S. Appl. No. 17/758,316, filed Jul. 1, 2022.
U.S. Appl. No. 17/759,697, filed Jul. 28, 2022.
U.S. Appl. No. 17/878,268, filed Aug. 1, 2022.
U.S. Appl. No. 17/907,125, filed Sep. 23, 2022.
U.S. Appl. No. 17/912,147, filed Sep. 16, 2022.
U.S. Appl. No. 17/929,887, filed Sep. 6, 2022.
U.S. Appl. No. 17/930,238, filed Sep. 7, 2022.
U.S. Appl. No. 17/933,590, filed Sep. 20, 2022.
U.S. Appl. No. 17/996,064, filed Oct. 12, 2022.
U.S. Appl. No. 17/996,155, filed Oct. 13, 2022.
U.S. Appl. No. 17/996,253, filed Oct. 14, 2022.
U.S. Appl. No. 17/996,468, filed Oct. 18, 2022.
U.S. Appl. No. 17/996,556, filed Oct. 19, 2022.
U.S. Appl. No. 18/003,029, filed Dec. 22, 2022.
U.S. Appl. No. 18/006,807, filed Jan. 25, 2023.
U.S. Appl. No. 18/007,105, filed Jan. 27, 2023.
U.S. Appl. No. 18/041,109, filed Feb. 9, 2023.
U.S. Appl. No. 18/042,842, filed Feb. 24, 2023.
U.S. Appl. No. 18/043,618, filed Mar. 1, 2023.
U.S. Appl. No. 18/115,444, filed Feb. 28, 2023.
U.S. Appl. No. 18/134,857, filed Apr. 14, 2023.
U.S. Appl. No. 18/140,163, filed Apr. 27, 2023.
U.S. Appl. No. 18/140,751, filed Apr. 28, 2023.
U.S. Appl. No. 18/164,800, filed Feb. 6, 2023.
U.S. Appl. No. 18/198,464, filed May 17, 2023.
U.S. Appl. No. 18/246,121, filed Mar. 21, 2023.
U.S. Appl. No. 18/247,986, filed Apr. 5, 2023.
U.S. Appl. No. 18/259,626, filed Jun. 28, 2023.
U.S. Appl. No. 18/260,122, filed Jun. 30, 2023.
U.S. Appl. No. 18/260,391, filed Jul. 5, 2023.
U.S. Appl. No. 18/260,394, filed Jul. 5, 2023.
U.S. Appl. No. 18/263,800, filed Aug. 1, 2023.
U.S. Appl. No. 18/264,004, filed Aug. 2, 2023.
U.S. Appl. No. 18/265,736, filed Jun. 7, 2023.
U.S. Appl. No. 18/299,788, filed Apr. 13, 2023.
U.S. Appl. No. 18/335,579, filed Jun. 15, 2023.
U.S. Appl. No. 18/373,424, filed Sep. 27, 2023.
U.S. Appl. No. 18/376,274, filed Oct. 3, 2023.
U.S. Appl. No. 18/389,009, filed Nov. 13, 2023.
U.S. Appl. No. 18/548,152, filed Aug. 28, 2023.
U.S. Appl. No. 18/549,387, filed Sep. 7, 2023.
U.S. Appl. No. 18/549,658, filed Sep. 8, 2023.
U.S. Appl. No. 18/553,625, filed Oct. 2, 2023.
U.S. Appl. No. 18/556,945, filed Oct. 24, 2023.
U.S. Appl. No. 18/558,502, filed Nov. 1, 2023.
U.S. Appl. No. 18/562,626, filed Nov. 20, 2023.
U.S. Appl. No. 18/563,672, filed Nov. 22, 2023.
U.S. Appl. No. 18/569,711, filed Dec. 13, 2023.
U.S. Appl. No. 18/569,778, filed Dec. 13, 2023.
U.S. Appl. No. 62/923,279, filed Oct. 18, 2019.
U.S. Appl. No. 62/926,767, filed Oct. 28, 2019.
U.S. Appl. No. 62/967,158, filed Jan. 26, 2020.
U.S. Appl. No. 62/991,754, filed Mar. 19, 2020.
U.S. Appl. No. 63/008,112, filed Apr. 10, 2020.
U.S. Appl. No. 63/094,646, filed Oct. 21, 2020.
U.S. Appl. No. 63/150,640, filed Feb. 18, 2021.
U.S. Appl. No. 63/191,558, filed May 21, 2021.
U.S. Appl. No. 63/192,289, filed May 24, 2021.
U.S. Appl. No. 63/230,897, filed Aug. 9, 2021.
U.S. Appl. No. 63/241,328, filed Sep. 7, 2021.
U.S. Appl. No. 63/308,190, filed Feb. 9, 2022.
U.S. Appl. No. 63/596,012, filed Nov. 3, 2023.
U.S. Appl. No. 63/608,553, filed Dec. 11, 2023.
*PureWick Corporation* v. *Sage Products, LLC* Transcripts vol. 2, Mar. 29, 2022.
*PureWick Corporation* v. *Sage Products, LLC* Transcripts vol. 3, Mar. 30, 2022.
*PureWick Corporation* v. *Sage Products, LLC* Transcripts vol. 4, Mar. 31, 2022.
*PureWick Corporation* v. *Sage Products, LLC* Transcripts vol. 5, Apr. 1, 2022.
*PureWick Corporation* v. *Sage Products, LLC* Transcripts vol. 1, Mar. 28, 2022.
"AMXD Control Starter Kit", Omni Medical Systems, Inc., 1 page.
"AMXDmax Advanced Mission Extender Device User & Maintenance Guide", Omni Medical, Jan. 11, 2010, 10 pages.
"AMXDmax Development History 2002-2014", Omni Medical Systems, Inc., 2 pages.
"Combat Force Multiplier in Flight Bladder Relief Cockpit Essential Equipment Brochure", Omni Medical, 20 pages.
"GSA Price List", Omni Medical, Apr. 2011, 2 pages.
"How is Polypropylene Fiber Made", https:www.yarnsandfibers.com/textile-resources/synthetic-fibers/polypropylene-fiber/polypropylene-fiber-production-raw-materials/how-is-polypropylene-fiber-made/ last accessed 2020, Oct. 7, 2020, 3 pages.
"Letter to Mark Harvie of Omni Measurement Systems", Department of Veterans Affairs, Nov. 1, 2007, 11 pages.
"Revised AMXDmax Advanced Mission Extender Device User & Maintenance Guide", Omni Medical Systems, Oct. 8, 2019, 52 pages.

(56) References Cited

OTHER PUBLICATIONS

Merriam-Webster Dictionary, "Embed Definition & Meaning", https://www.merriam-webster.com/dictionary/embed last accessed Aug. 3, 2023, 2003.

Pieper, et al., "An external urine-collection device for women: A clinical trial", Journal of ER Nursing, vol. 20, No. 2, Mar./Apr. 1993, pp. 51-55.

Vinas, "A Solution for an Awkward-But Serious-Subject", http://www.aero-news.net/index.cfm?do=main.textpost&id=69ae2bb1-838b-4098-a7b5-7flbb2505688 last accessed Feb. 8, 2021.

Hwang, et al., "Multifunctional Smart Skin Adhesive Patches for Advanced Health Care", Adv. Healthcare Mater, 2018, pp. 1-20.

Jagota, et al., "Adhesion, friction, and compliance of bio-mimetic and bio-inspired structured interfaces", Materials Science and Engineering, 2011, pp. 253-292.

Jeong, et al., "A nontransferring dry adhesive with hierarchical polymer nanohairs", PNAS, Apr. 7, 2009, pp. 5639-5644.

Jeong, et al., "Nanohairs and nanotubes: Efficient structural elements for gecko-inspired artificial dry adhesives", Science Direct, 2009, pp. 335-346.

Karp, et al., "Dry solution to a sticky problem", Nature., 2011, pp. 42-43.

Lee, et al., "Continuous Fabrication of Wide-Tip Microstructures for Bio-Inspired Dry Adhesives via Tip Inking Process", Journal of Chemistry, Jan. 2, 2019, pp. 1-5.

Macaulay, et al., "A Noninvasive Continence Management System: Development and Evaluation of a Novel Toileting Device for Women", The Wound, Ostomy and Continence Nurses Society, 2007, pp. 641-648.

Newman, et al., "The Urinary Incontinence Sourcebook", Petition for Interparties Review, 1997, 23 pages.

Newton, et al., "Measuring Safety, Effectiveness and Ease of Use of PureWick in the Management of Urinary Incontinence in Bedbound Women: Case Studies", Jan. 8, 2016, 11 pages.

Parmar, "10 Finalists Chosen for Dare-to-Dream Medtech Design Challenge (PureWick)", Design Services, Nov. 10, 2014, 3 pages.

Parness, et al., "A microfabricated wedge-shaped adhesive array displaying gecko-like dynamic adhesion, directionality", J.R. Soc. Interface, 2009, pp. 1223-1232.

\* cited by examiner

URINE COLLECTION SYSTEM INCLUDING A FLOW METER AND RELATED METHODS

CROSS-REFERENCE TO RELATED APPLICATIONS

This application claims priority to U.S. Provisional Patent Application No. 63/112,417 filed on Nov. 11, 2020, the disclosure of which is incorporated herein, in its entirety, by this reference.

BACKGROUND

An individual may have limited or impaired mobility such that typical urination processes are challenging or impossible. For example, the individual may have surgery or a disability that impairs mobility. In another example, the individual may have restricted travel conditions such as those experience by pilots, drivers, and workers in hazardous areas. Additionally, fluid collection from the individual may be needed for monitoring purposes or clinical testing.

Bed pans and urinary catheters, such as a Foley catheter, may be used to address some of these circumstances. However, bed pans and urinary catheters have several problems associated therewith. For example, bed pans may be prone to discomfort, spills, and other hygiene issues. Urinary catheters be may be uncomfortable, painful, and may cause urinary tract infections.

Thus, users and manufacturers of urine collection devices continue to seek new and improved devices, systems, and methods to collect urine.

SUMMARY

Embodiments disclosed herein are related to urine collection devices and methods of using urine collection devices. In an embodiment, a urine collection system includes a urine collection device configured to collect urine discharged from a user and a urine collection container in fluid communication with the urine collection device and sized and dimensioned to receive the urine discharged from the user. The urine collection system also includes a flow meter having a communication interface and positioned between the urine collection container and the urine collection device. The flow meter is configured to detect a flow property of the urine at least related to a volume of the urine entering the urine collection container and the communication interface is configured to wirelessly communicate to a computing device at least one of the detected flow property or the volume of the urine including the volume of the urine discharged from the user entering the urine collection container.

In an embodiment, a method of determining a volume of urine discharged by a user includes receiving urine discharged from the user in a urine collection device. The method also includes detecting, with a flow meter, a flow property of the urine at least related to a volume of the urine discharged by the user as the urine is passed from the urine collection device to a urine collection container. The method also includes wirelessly transmitting, from a communication interface of the flow meter to a computing device, at least one of the detected flow property or the volume of the urine including the volume of the urine.

Features from any of the disclosed embodiments may be used in combination with one another, without limitation. In addition, other features and advantages of the present disclosure will become apparent to those of ordinary skill in the art through consideration of the following detailed description and the accompanying drawings.

BRIEF DESCRIPTION OF THE DRAWINGS

The drawings illustrate several embodiments of the present disclosure, wherein identical reference numerals refer to identical or similar elements or features in different views or embodiments shown in the drawings.

DETAILED DESCRIPTION

Embodiments disclosed herein are related to fluid collection systems including an automated urine output (AUO) measurement, and methods of using the same. The devices and systems disclosed herein are configured to collect fluids from an individual and include a flow meter. The fluids collected by the urine collection devices may include at least one of urine, vaginal discharge, penile discharge, reproductive fluids, blood, sweat, or other bodily fluids. Embodiments of urine collection systems disclosed herein may include a flow meter configured to detect and wirelessly transmit a flow property of the urine to a computing device. The flow property of the urine may be related at least to a volume of the urine exiting the urine collection device and/or entering the urine collection container. In some embodiments, the flow property may include at least one of a volume, a mass, or a velocity of the urine passing through or proximate to the flow meter. For example, the flow property may include a flow rate of the urine over a predetermined period of time. At least one of the flow meter or the computing device may be configured to translate the flow property of the urine detected by the flow meter into one or more volumetric measurement(s) of urine exiting the urine collection device and/or entering the urine collection container. By detecting and wirelessly transmitting the flow property and/or the volume of the urine detected by the flow meter, one or more embodiments of the fluid collection systems described herein may determine, collect, and/or utilize (in real-time) more accurate volumetric flow rates and urine discharge information.

In some examples, the flow property of the urine detected by the flow meter in the urine collection system may allow the fluid collection systems to be used with a variety of patient demographics, including ambulatory patients that need urine flow rates monitored when asleep or patients confined to beds. The computing device or system receiving at least one of the detected flow property or the volume of the urine detected by the flow meter may determine trends in urine discharge by a patient. The computing device or system receiving at least one of the detected flow property or the volume of the urine detected by the flow meter may automatically push the received flow property and/or volume of the urine to other health applications, such as a hospital electronic medical records system. As shall be described in greater detail herein, the flow meter may be positioned in-line with a tube connecting a urine collection device and a urine collection container or may be secured or securable to a urine collection device between the urine collection device and a urine collection container. Systems and methods described herein may allow caregivers to bypass the steps of measuring urine discharged by a user and charting data pertaining to the volume of urine discharged by the user.

Figure 1A:
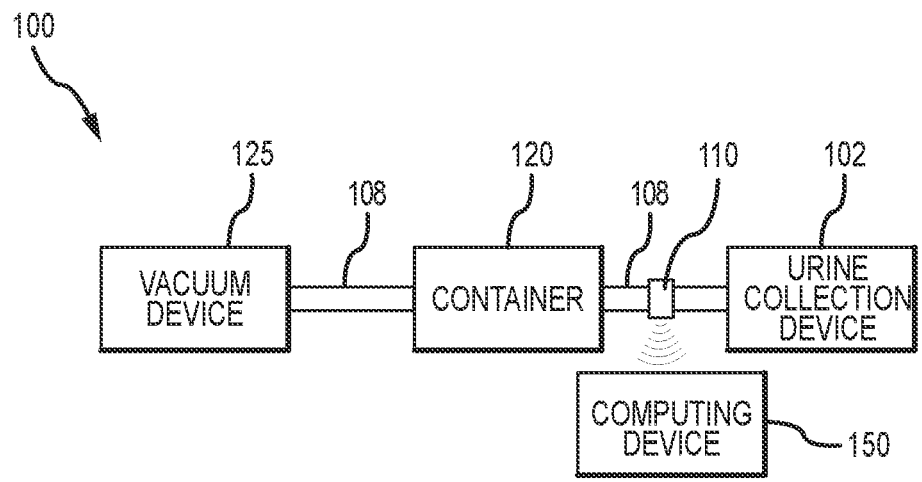
FIG. 1A is a block diagram of a urine collection system including a flow meter, according to an embodiment.

FIG. 1A is a block diagram of a urine collection system 100, according to an embodiment. The urine collection system 100 includes a fluid (e.g., urine) collection device 102, a conduit 108, a fluid (e.g., urine) storage container 120, a vacuum device 125, and a flow meter 110. The urine collection device 102 may include a male or female urine collection device. PCT International Application No. PCT/US2019/029616, for example, describes various embodiments of both male and female urine collection devices, the disclosure of which is incorporated in its entirety by this reference. Moreover, the urine collection device 102 may be interchangeable in the urine collection system 100 between different types, varieties, and sizes of male or female urine collection devices. The urine collection device 102 is configured to be positioned proximate or adjacent to a urethra of a user. Generally, the urine collection device 102 may include a surface sized to be positioned proximate or adjacent to the urethra and configured to wick urine or other fluids away from the user. Urine or other fluids may be wicked from the surface to a reservoir in the urine collection device 102.

The conduit 108 may include a flexible material such as plastic tubing (e.g., medical tubing). Such plastic tubing may include a thermoplastic elastomer, polyvinyl chloride, ethylene vinyl acetate, polytetrafluoroethylene, etc., tubing. In some embodiments, the conduit 108 may include silicone or latex. The urine collection device 102, the container 120, and the vacuum source 125 may be fluidly coupled to each other via one or more conduits 108. For example, urine collection device 102 may be operably coupled to one or more of the urine storage container 120 or the vacuum device 125 via the conduit 108. Fluid (e.g., urine or other bodily fluids) collected in the urine collection device 102 may be removed from the urine collection device 102 via the conduit 108 secured to the urine collection device 102. Suction force may be introduced into the chamber of the urine collection device 102 via the inlet of the conduit 108 responsive to suction (e.g., vacuum) force applied at the outlet of the conduit 108.

The suction force may be applied to the outlet of the conduit 108 by the vacuum device 125 either directly or indirectly. The suction force may be applied indirectly via the urine storage container 120. For example, the outlet of the conduit 108 may be connect to or disposed within the urine storage container 120 and an additional conduit 108 may extend from the urine storage container 120 to the vacuum device 125. Accordingly, the vacuum device 125 may apply suction to the urine collection device 102 via the urine storage container 120. The suction force may be applied directly via the vacuum device 125. For example, the outlet of the conduit 108 may be disposed within the vacuum device 125. An additional conduit 108 may extend from the vacuum device 125 to a point outside of the urine collection device 102, such as to the urine storage container 120. In such examples, the vacuum device 125 or other pump may be disposed between the urine collection device 108 and the urine storage container 120.

The urine storage container 120 is sized and shaped to retain a fluid therein. The urine storage container 120 may include a bag (e.g., drainage bag), a bottle or cup (e.g., collection jar), or any other enclosed container for storing bodily fluid(s) such as urine. In some examples, the conduit 108 may extend from the urine collection device 102 and attach to the urine storage container 120 at a first point therein. An additional conduit 108 may attach to the urine storage container 120 at a second point thereon and may extend and attach to the vacuum device 125. Accordingly, a vacuum (e.g., suction) may be drawn through urine collection device 102 via the urine storage container 120. Fluid, such as urine, may be drained from the urine collection device 102 using the vacuum device 125.

The vacuum device 125 may include one or more of a manual vacuum pump, and electric vacuum pump, a diaphragm pump, a centrifugal pump, a displacement pump, a magnetically driven pump, a peristaltic pump, or any pump configured to produce a vacuum. The vacuum device 125 may provide a vacuum or suction to remove fluid from the urine collection device 125. In some examples, the vacuum device 125 may be powered by one or more of a power cord (e.g., connected to a power socket), one or more batteries, or even manual power (e.g., a hand operated vacuum pump). In some examples, the vacuum device 125 may be sized and shaped to fit outside of, on, or within the urine collection device 102. For example, the vacuum device 125 may include one or more miniaturized pumps or one or more micro pumps.

The urine collection system 100 also includes a flow meter 110 configured to detect a flow property of the urine at least related to a volume of the urine pulled from the urine collection device 102 and passing through conduit 108 before entering the urine storage container 120. In some embodiments, the flow meter 110 is secured or securable between urine collection device 102 and the urine storage container 120 such that a first portion of the conduit 108 extends between the urine collection device 102 and the flow meter 110 and a second portion of the conduit 108 extends between the flow meter 110 and the urine storage container 120. In some embodiments, the flow meter 110 is secured or securable directly to the urine collection device 102, i.e. the conduit 108 extends between the flow meter 110 and the urine storage container, but a conduit or tubing is absent between the urine collection device 102 and the flow meter 110. In some embodiments, the flow meter 110 is secured or securable directly to the urine storage container 120, i.e. the conduit 108 extends between the urine collection device 102 and the flow meter 110, but a conduit or tubing is absent between the flow meter 110 and the urine storage container 120.

The flow meter 110 may include any suitable flow meter configured to detect a flow property of the urine that may be used to determine a volume of the urine passing through or within a predetermined proximity to the flow meter 110. The flow property detected by the flow meter 110 may include at least one of a volume, a mass, or a velocity of the urine passing through or proximate to the flow meter 110. In some embodiments, the flow meter may include a positive displacement flow meter configured to directly measure the actual volume of the urine passing through the flow meter. In some embodiments, the flow meter is configured to detect a mass or a velocity of the urine passing through or proximate to the flow meter 110, which mass or velocity may be translated (by at least one of the flow meter 110 or the computing device 150) into a volume or flow rate. The flow meter 110 may detect a duration of time during which urine is passing through or within a predetermined proximity to the flow meter 110. In some embodiments, the flow meter 110 or other computing device may then calculate that volume of the urine that has passed the flow meter 110 based on a known cross-sectional area or volume of the conduit 108 or the flow meter 110.

In some embodiments, the flow meter 110 may mechanically or ultrasonically detect the flow property of the urine passing between the urine collection device 102 and the urine collection container 120. For example, at least a portion of the flow meter 110 may be in line with the conduit 108 effective to allow the flow meter 110 to mechanically detect the flow property of the urine through the conduit 108. In some embodiments, at least a portion of the flow meter 110 extends into the conduit 108 effective to allow the flow meter 110 to mechanically detect the flow property of the urine through the conduit 108. The flow meter 110 may include at least one of a bi-rotor, a disc, a piston, a propeller, a paddle wheel, and/or a rotameter. In some embodiments the flow meter 110 may include laminar or venturi flow meter. In some embodiments, the flow meter 110 may be detachably or fixedly secured or securable to the outside of the conduit 108 and ultrasonically (i.e., via the Doppler effect) or electromagnetically detect the flow property of the urine through the conduit 108. Detachable securement of the flow meter 110 to the conduit 108 allows the flow meter to be reused with multiple conduits 108 and/or users. For example, a Doppler ultrasonic flow meter may be secured or securable outside of the conduit 108 and be reused on multiple urine collection systems. In some embodiments, the flow meter 110 may include system of valves configured to close off the fluid collection container 120 at a certain, predetermined volume and only allow that predetermined volume to be withdrawn from the urine collection device 102.

The flow meter 110 also may include a communication interface configured to wirelessly communicate to a computing device 150 separate or external to the flow meter 110. For example, the flow meter 110 may be configured to wirelessly communicate via BLUETOOTH or WI-FI to the computing device 150 data including at least one of the detected flow property or the volume of the urine discharged from the user and entering the fluid collection container 120. In some embodiments, the flow meter 110 is configured to wirelessly communicate the volumetric flow data to the computing device 150 in predetermined intervals or whenever urine flow is detected. The computing device 150 may include various computing devices configured to wirelessly communicate with the flow meter 110. For example, the computing device 150 may include a smartphone, a tablet computer, a desktop computer, or medical computing devices found in hospital or healthcare rooms. In some embodiments, the flow meter 110 is configured to wirelessly communicate the flow property of the urine to the computing device 150 which includes a software application configured to record the data including the flow property of the urine, display the flow property and/or volume of the urine discharged by the user 50, and/or determine and display trends and totals related to the flow property and/or volume of the urine discharged by the user. The computing device 150 may be located on the user, in a hospital room, in a home of the user, or combinations thereof. Additional details regarding the schematics and wireless communications of the flow meter 110 and the computing device 150 are provided below in reference to FIG. 5.

At least one of the flow meter 110 or the computing device 150 may be configured to automatically translate data of the flow property into a volume measurement, such as the volume of urine discharged by a user over a predetermined period of time (such as an hour or a day). Data including volume measurements transmitting to the computing device 150 may be recorded and/or pushed to an electronic medical record (EMR) system for future reference and consideration. At least one of the flow meter 110 or the computing device 150 may provide the volume of urine entering the urine collection device 102 in real-time using the data detected and/or communicated by the flow meter 110. The computing device 150 may transmit or signal an alert when a predetermined volume of fluid is discharged by the user. The computing device 150 may be configured to determine and provide trends in the volume of urine discharged by the user.

Figure 1B:
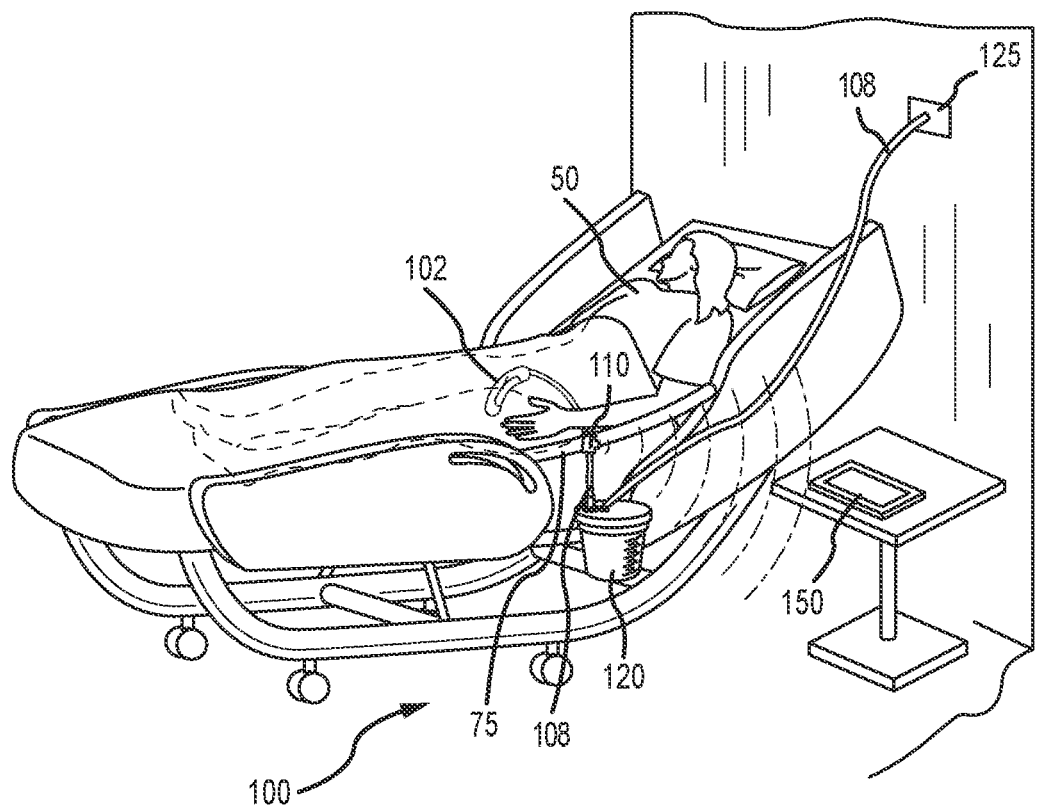
FIG. 1B is an isometric view of the urine collection system of FIG. 1A in use, according to an embodiment.

FIG. 1B shows a urine collection system 100 in use in a hospital room environment, according to an embodiment. Although the user 50 is shown lying down in FIG. 1B, in some embodiments, the user 50 may be ambulatory during use of the urine collection system 100. The urine collection device 102 shown in FIG. 1B includes a female urine collection device positioned adjacent or proximate to the urethra of the user 50. In some embodiments, the urine collection device 102 may include a male urine collection device positioned over a male urethra or having at least a portion of a penis inserted therein. The vacuum device 125 shown in FIG. 1B includes a wall-mounted device or wall-connected vacuum source. In some embodiments, the vacuum device 125 may include a portable or modular vacuum device or pump. The computing device 150 shown in FIG. 1B includes a bedside computing device or table computing device. In some embodiments, the computing device 150 may include any computing device configured to wirelessly communicate with the flow meter 110.

The flow meter 110 shown in FIG. 1B includes a flow meter attached to the conduit 108 and in-line with the conduit 108 such that a first portion of the conduit 108 extends between the urine collection device 102 and the flow meter 110 and a second portion of the conduit 110 extends between the flow meter 110 and the urine storage container 120. In some embodiments, the flow meter 110 may include any of the flow meters described above in any of the positions described above. The flow meter 110 also may be configured to detachably secure to a portion of a bed, such as an arm or frame 75 of the bed. The urine storage container 120 also may be configured to detachably secure to a portion of the bed, such as an arm or frame 75 of the bed.

In use, the user 50 may void or discharge urine into the urine collection device 102. The vacuum device 125 may pull a vacuum on the urine collection device 102 effective to pull urine discharged into the urine collection device 102 through the conduit 108 and into the urine storage container 120. As the urine is pulled from the urine collection device 102 and into the urine storage container 120, the flow meter 110 detects the flow property of the urine at least related to the volume of the urine passing from the urine collection device 102 to the urine storage container 120. The flow meter 110 may then wirelessly transmit or communicate to the computing device 150 data including the flow property of the urine at least related to the volume of the urine passing from the urine collection device 102 to the urine storage container 120.

Figure 1C:
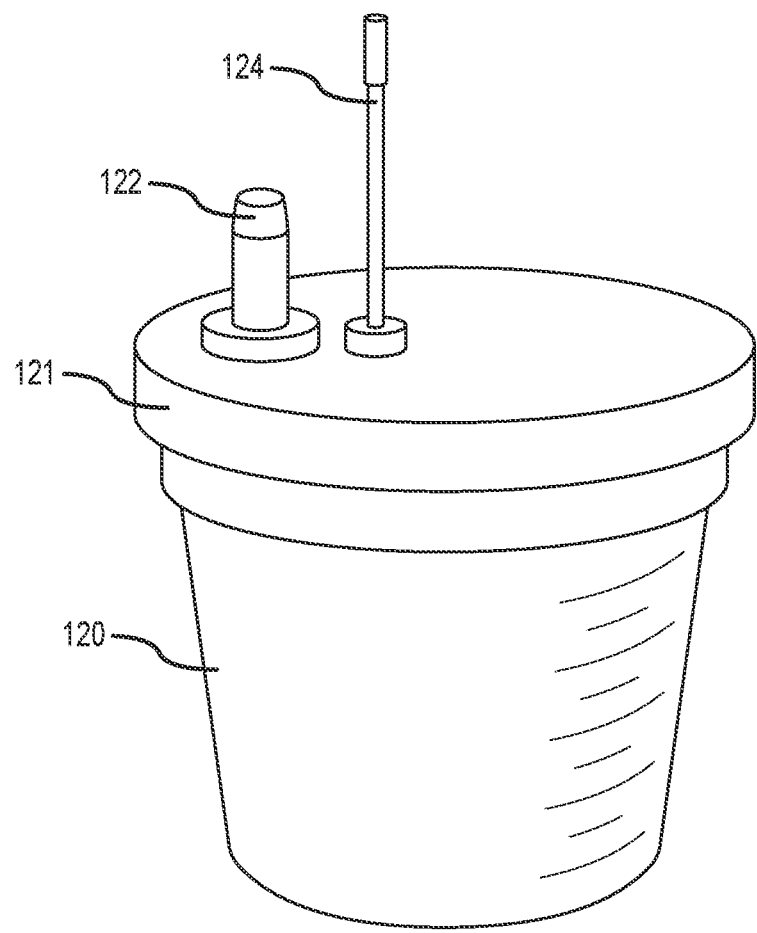
FIG. 1C is an isometric view of a urine collection container, according to an embodiment.

FIG. 1C shows a urine storage container 120 used in a urine collection system 100, according to an embodiment. The urine storage container 120 may be substantially rigid effective to allow a vacuum to be pulled on the urine collection device 102 and the conduit 108 through the urine storage container 120. The urine storage container 120 may include a lid 121 having multiple ports. For example, the lid 121 may include a vacuum port 124 configured to secure to a conduit 108 in fluid communication with the vacuum device 125 such that the vacuum device 125 can pull a vacuum on the interior region of the urine storage container 120 through the vacuum port 124. The lid 124 may include a urine collection port 122 configured to secure to a conduit 108 in fluid communication with an interior region of the urine collection device 125 such that a vacuum pulled on the interior region of the urine storage container 120 pulls a vacuum on the interior region of the urine collection device 102 effective to pull urine in the urine collection device 102 through the conduit 108, pass the flow meter 110, and into the interior region of the storage container 120.

Figure 2A:
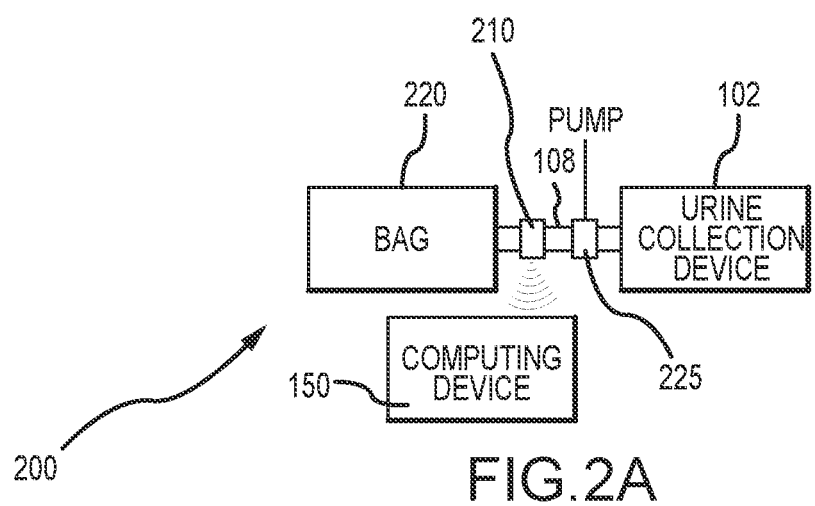
FIG. 2A is a block diagram of a urine collection system including a flow meter, according to an embodiment.

FIG. 2A is a block diagram of a urine collection system 200, according to an embodiment. Unless otherwise noted, the urine collection system 200 may include any aspect of the urine collection device 100 described above, such as the urine collection device 102, the conduit 108, and the computing device 150. The urine collection system 200 also may include a fluid storage bag 220, a flow meter 210, and a pump 225 positioned in-line with the conduit 108. The flow meter 210 is configured to wirelessly communicate with the computing device 150. The conduit 108 may fluidly connect the urine collection device 102 and the bag 220. The pump 225 may be positioned between the urine collection device 102 and the fluid storage bag 220. In some embodiments, the pump 225 is positioned between the urine collection device 102 and the flow meter 210. In some embodiments, the pump 225 is positioned between the flow meter 210 and the fluid storage bag 220.

The pump 225 of the urine collection system 200 may include any of a variety of pumps, such as a diaphragm pump. The pump 225 may include multiple flow rates that allow a user or wearer to select a desired or preferred flow rate. The pump 225 may include a removable or modular pump that may allow a user to remove the pump 225 and attach a different pump to the urine collection system 200. The pump 225 also may include a portable or modular pump that is transportable by a user or wearer. For example, the pump 225 may be sized to carry in a backpack or attach to the user or clothing of a user. The pump 225 may include a height of less than about 2.5 cm, a width of less than about 2.5 cm, and a depth of less than about 1.3 cm. The pump 225 also is configured to pull a vacuum in the conduit 108 to pull fluid from the urine collection device 102. The pump 225 also may be configured force fluid through the conduit 108 into the collection bag 220.

The urine collection system 200 also may include a power supply (not shown). The power supply may be a modular power supply that is detachable from the urine collection system 100 and replaceable with a similar or different power supply. For example, a user may be plan to engage in a longer ambulatory activity, and therefore desire a longer lasting power supply. A user also may desire to switch an initial power supply to a new power supply when the initial power supply is depleted. In some embodiments, the power supply is built into the pump 225 and/or the flow meter 210.

That is, the pump 225 and/or the flow meter 210 may include a housing or compartment for the power supply. In some embodiments, the power supply may be external to the pump 225 and/or the flow meter 210, but may be electrically coupled to the pump 225 and/or the flow meter 210 such that the power supply may selectively power the pump 225 and/or the flow meter 210. The power supply may include one or more batteries, such as rechargeable batteries. The power supply also may include a wire and plug configured to plug into a wall outlet. In some embodiments, the power supply may include one or more rechargeable batteries and a wire and plug configured to charge the one or more rechargeable batteries.

The urine collection system 200 also includes a fluid storage bag 220. The fluid storage bag 220 may be a collapsible or expandable bag. For example, the fluid storage bag 220 may be generally flat when empty, but may expand when urine or other fluid is forced into the fluid storage bag 220. In some embodiments, the urine storage container 120 described above may replace the fluid storage bag 220 in the urine collection system 200.

Figure 2B:
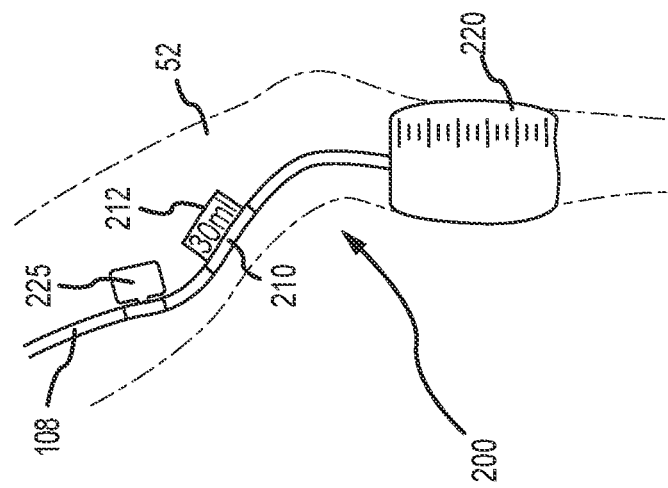
FIG. 2B is a side view of the urine collection system of FIG. 1B in use, according to an embodiment.

FIG. 2B shows a portion of the urine collection system 200 in use, according to an embodiment. In some embodiments, the fluid storage bag 220 may be configured to secure to a portion of the body of the user, such as the leg 52. The fluid storage bag 220 may include straps or other elements configured to detachably secure the fluid storage bag to the user 50. The conduit 108 may be sized and dimensioned to extend between the urine collection device 102 (not shown in FIG. 2B) and the urine storage bag 220. For example, the conduit 108 may be sized and dimensioned to extend from the pubic region of the user 50 and down at least a portion of the leg 52 of the user 50 to the fluid storage bag 220 secured or securable to the leg 52.

The urine collection system 200 includes a flow meter 210. Unless otherwise noted, the flow meter 210 may include any aspect of the flow meter 110. The flow meter 210 may include a display 212 that displays a volume of urine detected by the flow meter 210 over a selected period of time. For example, the display 212 may display the volume of urine detected by the flow meter 210 until the flow meter 210 is reset to zero. In some embodiments, the display 212 is configured to display the volume of urine detected by the flow meter 210 during a period of time such as an hour, multiple hours, a day, multiple days, and so on. In some embodiments, the flow meter 210 may allow the user 50 or care worker to select the period of time elapsed before the volume displayed on the display 212 resets to zero. In some embodiments, the flow meter 110 may replace the flow meter 210.

In some embodiments, the pump 225 may be positioned in-line with the conduit 108 between urine collection device 102 and the flow meter 210, shown in FIG. 2B. In other embodiments, the pump 225 may be positioned in-line with the conduit 108 between the flow meter 210 and the fluid storage bag 220.

In use, the user 50 may void or discharge urine into the urine collection device 102. The pump 225 may pull urine from the urine collection device 102 through the conduit 108 and into the fluid storage bag 220. In some embodiments, the urine collection system 200 may be used with a female urine collection device. As the urine is pulled from the urine collection device 102 and into the fluid storage bag 220, the flow meter 210 detects the flow property of the urine at least related to the volume of the urine passing from the urine collection device 102 to the fluid storage bag 220. The flow meter 210 may then wirelessly transmit or communicate to the computing device 150 data including the flow property of the urine at least related to the volume of the urine passing from the urine collection device 102 to the fluid storage bag 220.

Figure 2C:
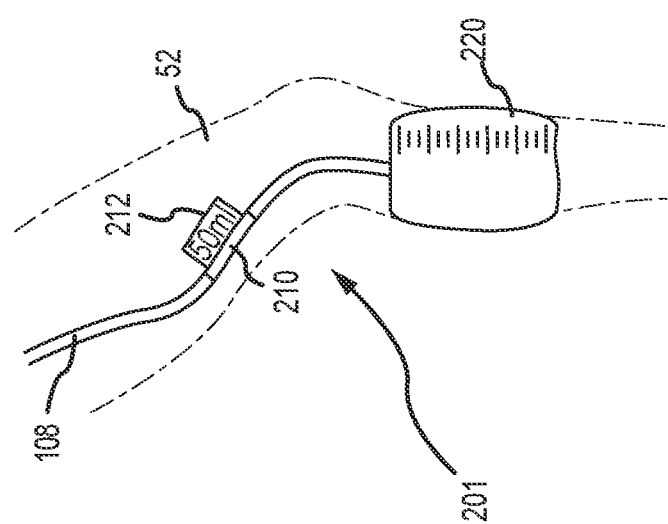
FIG. 2C is a side view of a urine collection system in use, according to an embodiment.

FIG. 2C shows an embodiment of a urine collection system 201, according to an embodiment. Unless otherwise noted, the urine collection system 201 may include any aspect of the urine collection system 200. In some embodiments, the urine collection system 201 may include a urine collection device 102 (not shown in FIG. 2C), the conduit 108, the flow meter 210, and the fluid storage bag 220, while the pump 225 may be absent from the urine collection system 201. In use, the user 50 may void or discharge urine into the urine collection device 102. Gravity may then pull urine from the urine collection device 102 through the conduit 108 and into the fluid storage bag 220. In some embodiments, the urine collection system 201 may be used with a male urine collection device 102. As the urine is pulled or otherwise forced from the urine collection device 102 and into the fluid storage bag 220, the flow meter 210 detects the flow property of the urine at least related to the volume of the urine passing from the urine collection device 102 to the fluid storage bag 220. The flow meter 210 may then wirelessly transmit or communicate to the computing device 150 data including the flow property of the urine at least related to the volume of the urine passing from the urine collection device 102 to the fluid storage bag 220.

Figure 3A:
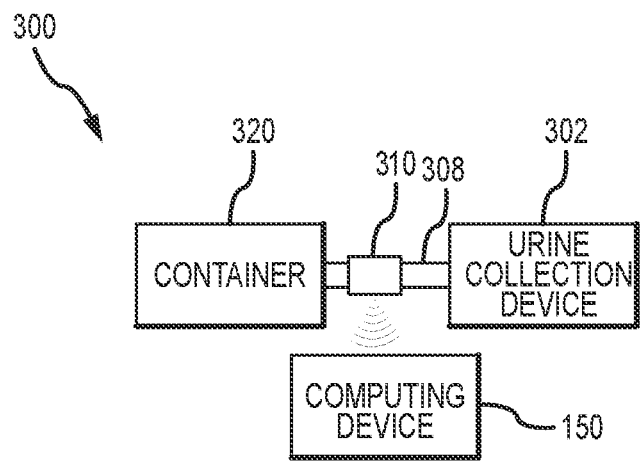
FIG. 3A is a block diagram of a urine collection system including a flow meter, according to an embodiment.

FIG. 3A is a block diagram of a urine collection system 300, according to an embodiment. Unless otherwise note, the urine collection system 300 can include any aspect of the urine collection systems 100, 200 described above, such as the computing device 150. The flow meter 310 is configured to wirelessly communicate with the computing device 150. The urine collection system 300 also may include a urine storage container 320 and a urine collection device 302 in fluid communication with the urine storage container 320. The flow meter 310 may be positioned between at least a portion of the urine collection device 302 and at least a portion of the fluid storage 320.

Figure 3B:
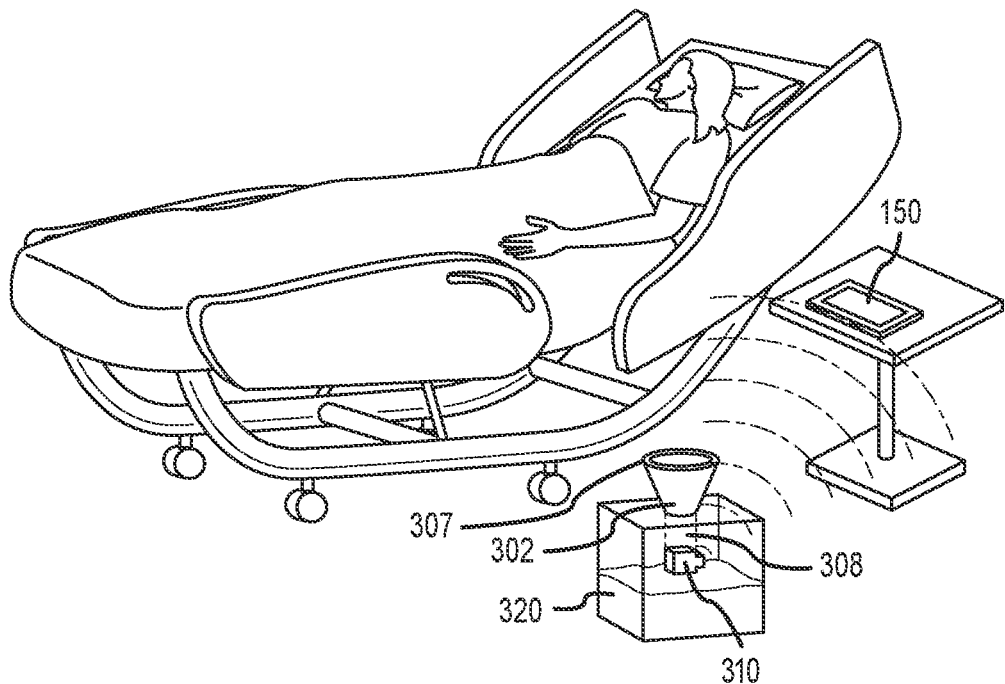
FIG. 3B is an isometric view of the urine collection system of FIG. 3B, according to an embodiment.

FIG. 3B shows the urine collection system 300 in use in a hospital room setting, according to an embodiment. In some embodiments, the urine collection system 300 may be used in a bathroom setting or a home room setting. The urine collection device 302 may include a funnel-shaped fluid or bowl-shaped urine collection device having wide end 307 and narrow end 308 distal to the wide end 307. In some embodiments, the urine collection device 302 may include a fluid collection seat. For example, a fluid collection seat may include a wide end 307 having a size that allows a user 50 to sit on the fluid collection seat to urinate into the fluid collection seat. The urine collection device 302 also may be sized and dimensioned to a man or woman to urinate into the urine collection device from a standing position.

The flow meter 310 is configured to wirelessly communicate with the computing device 150 and, unless otherwise noted, may include any aspect of the flow meters 110, 210. For example, although not shown in FIG. 3B, the flow meter 310 may include the display 212 of the flow meter 210. Moreover, the flow meter 310 may include be configured to detect flow properties of the urine at least related to the volume as described above in relation to the flow meters 110, 210. For example, the flow meter 310 may be configured to detect a flow property of the urine at least related to the volume of urine as urine passes or moves from the urine collection device 302 to the urine storage container 320.

The flow meter 310 may be fixedly or detachably secured or securable to a portion of the urine collection device 302. For example, the flow meter 310 may be fixedly or detachably secured or securable proximate to the narrow end 308 of the urine collection device 302. In some embodiments, the flow meter 310 is fixedly or detachably secured or securable to the narrow end 308 such that the urine collection device 302 does not extend beyond the flow meter 310. In some embodiments, the flow meter 310 is fixedly or detachably secured or securable to urine collection device 302 at least partially between the narrow end 308 and the wide end 307. In some embodiments, the flow meter 310 may be detachably secured or securable to the urine collection device 302 with one or more of a threaded fastening, clips, or friction fit.

The urine storage container 320 is configured to receive urine discharged by the user 50 into the urine collection device 302 after the flow meter 310 has detected the flow property of the urine at least related to the volume of the urine discharged into the urine collection device 302. At least a portion of the urine storage container 320 may be positioned below the urine collection device 302 such that gravity pulls the from the urine collection device 302 into the urine storage container 320. In some embodiments, the urine storage container includes one or more supports configured to support at least a portion of the urine collection device 302 when a user is sitting on and/or urinating in the urine collection device 302. The one or more supports may include a layer or one or more support bars through which at least a portion of the urine collection device 302 extends, such as the narrow end 308. The urine storage container 320 may be sized and dimensioned to allow a user or caregiver to carry or otherwise transport the urine storage container 320 to the toilet or disposal area after the user has discharged urine into the urine storage container 320 through the urine collection device 302.

In some embodiments, the urine storage container 320 includes a toilet (not shown). For example, the urine collection device 302 may be sized and dimensioned to position on conventional toilets within contact the water in the toilets. The urine collection device 302, then, may be sized and dimension to rest on a toilet seat and support a user sitting on the wide end 307 of the urine collection device 302 while the urine collection device 302 is resting on the toilet seat. Urine discharged into the urine collection device 302 resting on the toilet seat may flow to the narrow end 308 of the urine collection device and the flow property of the urine may be measured by the flow meter 310 as the urine is passing from the urine collection device 302 to the toilet.

Figure 4:
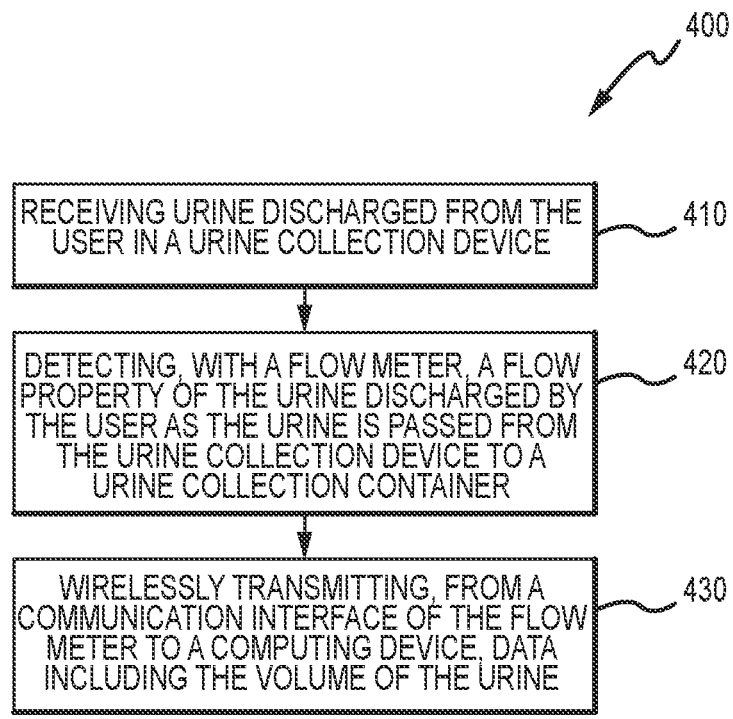
FIG. 4 is a flow diagram of a method of determining a volume of liquid discharged by a user.

FIG. 4 is a flow diagram of a method 400 of determining a volume of urine discharged by a user, according to an embodiment. The method 400 may include an act 410 of receiving urine discharged from the user in a urine collection device. The method 400 also may include an act 420 of detecting, with a flow meter, a flow property of the urine at least related to a volume of the urine discharged by the user as the urine is passed from the urine collection device to a urine collection container. The method 400 also may include an act 430 of wirelessly transmitting, from a communication interface of the flow meter to a computing device, data including at least the flow property of the urine related to a volume of the urine.

The act 410 may include receiving urine discharged from the user in a urine collection device, such as urine collection device 102. Accordingly, in some embodiment, the act 410 may include receiving the urine discharged from the user in a urine collection device positioned proximate to a urethra of the user. In some embodiments, the method 400 also may include an act of pulling a vacuum on a first conduit in fluid communication with the urine collection device effective to draw urine from the urine collection device through the first conduit and into the urine collection container, with the flow meter being secured to the first conduit. In some embodiments, the method 400 may include an act of pulling a vacuum on the first conduit in fluid communication with the urine collection device and a second conduit in fluid communication with the first conduit and the urine collection container effective to draw the urine from the urine collection device through the first conduit, the flow meter, and the second conduit into the urine collection container, with the flow meter being secured to the second conduit between the first conduit and the second conduit.

In some embodiments, the act 410 may include receiving urine discharged from the user in the urine collection device 302. Accordingly, the act 410 may include receiving the urine discharged from the user in a funnel-shaped urine collection device having a wide end and a narrow end. In some embodiments, the method 400 also may include positioning the funnel-shaped urine collection seat on the urine collection container.

The act 420 may include detecting, with a flow meter, the flow property of the urine at least related to a volume of the urine discharged by the user as the urine is passed from the urine collection device to a urine collection container. In some embodiments, the act 420 includes detecting, with the flow meter secured to the narrow end of the funnel-shaped urine collection device, the flow property of the urine discharged by the user as the urine is passed from the urine collection device to the urine collection container. In some embodiments, the method 400 may include an act of regulating the volume of the urine passing through the flow meter. In some embodiments, the method 400 may include an act of displaying, on a display on the flow meter, the volume of the urine entering the urine collection container during a selected period of time.

The act 430 may include wirelessly transmitting, from a communication interface of the flow meter to a computing device, data including the flow property of the urine at least related to the volume of the urine. In some embodiments, the method 400 also includes an act of providing, with the computing device, the volume of urine entering the urine collection device in real-time using the data communicated by the flow meter. In some embodiments, the method 400 also includes an act of transmitting, with the computing device, the data communicated by the flow meter including the volume of the urine to an electronic medical record system.

The acts of the method 400 described above, including the acts 410, 420, and 430, are for illustrative purposes. For example, acts of the method 400, including the acts 410, 420, and 430, can be performed in different orders, split into multiple acts, modified, supplemented, or combined. In an embodiment, acts of the method 400, including the acts 410, 420, and 430, can be omitted from the method 400. Any of the acts of the method 400, including the acts 410, 420, and 430, can include using any of the urine collection systems disclosed herein.

Figure 5:
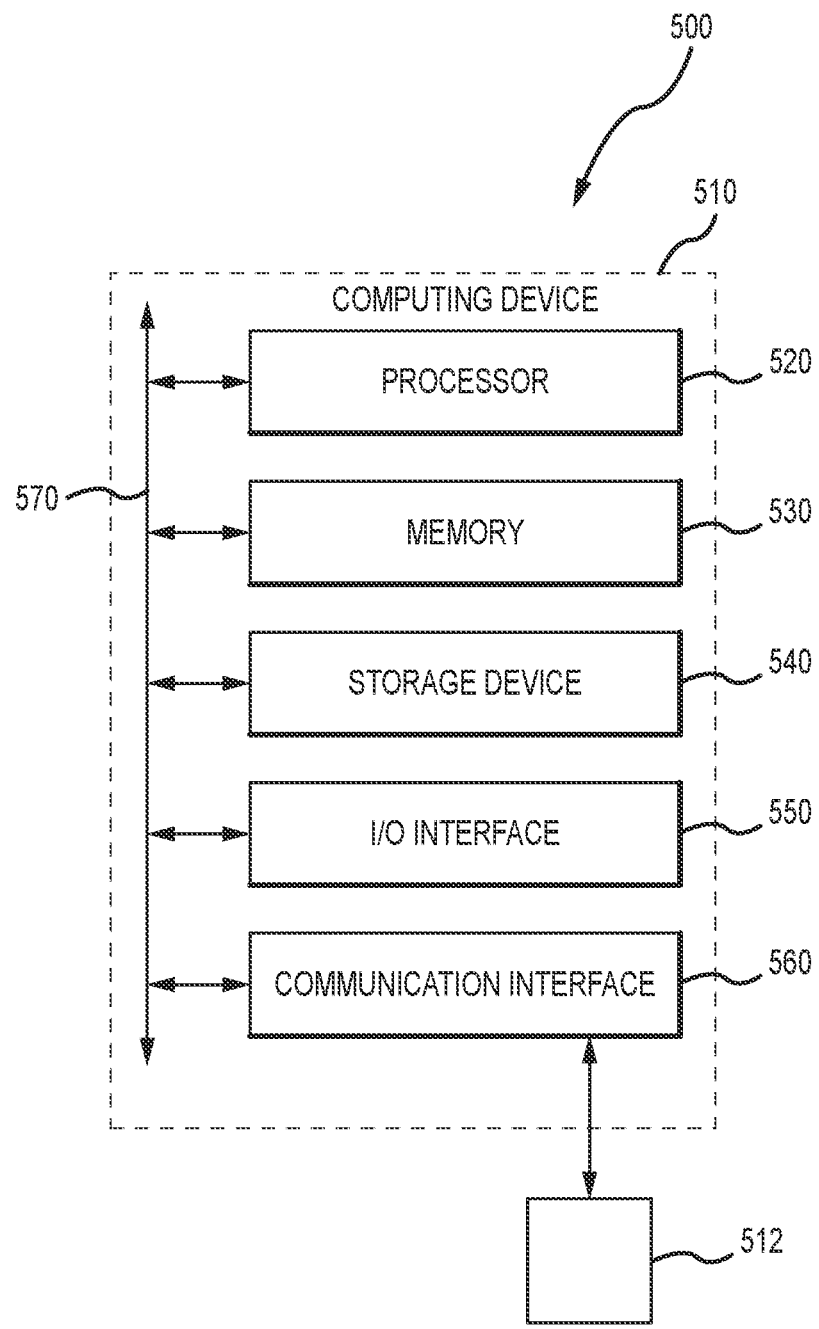
FIG. 5 is a schematic for a computing device in a flow meter of a urine collection system, according to an embodiment.

Any of the example urine collection systems 100, 200, 201, 300 disclosed herein may be used to carry out any of the example methods 400 disclosed herein. FIG. 5 is a schematic of a controller 500 that may be included in any of the flow meters 110, 210, 310 or the computing device 150 described herein, according to an embodiment. The controller 500 may be configured to implement one or more acts any of the example methods disclosed herein, such as the act 430 of the method 400 of wirelessly transmitting, from a communication interface of the flow meter to a computing device, data including the flow property of the urine at least related to a volume of the urine.

The controller 500 includes at least one computing device 510. The at least one computing device 510 is an exemplary computing device that may be configured to perform one or more of the acts described above, such as the act 430 of the method 400. The computing device 510 can comprise at least one processor 520, memory 530, a storage device 540, an input/output ("I/O") device/interface 550, and a communication interface 560. While an example computing device 510 is shown in FIG. 5, the components illustrated in FIG. 5 are not intended to be limiting of the controller 500 or computing device 510. Additional or alternative components may be used in some examples. Further, in some examples, the controller 500 or the computing device 510 can include fewer components than those shown in FIG. 5. For example, in some embodiments the controller 500 in the flow meter 110, 210, 310 may include only the communication interface 560 described below. Components of computing device 510 shown in FIG. 5 are described in additional detail below.

In some examples, the processor(s) 520 includes hardware for executing instructions (e.g., instructions for carrying out one or more portions of any of the methods disclosed herein), such as those making up a computer program. For example, to execute instructions, the processor(s) 520 may retrieve (or fetch) the instructions from an internal register, an internal cache, the memory 530, or a storage device 540 and decode and execute them. In particular examples, processor(s) 520 may include one or more internal caches for data such as flow property and flow rate tables. As an example, the processor(s) 520 may include one or more instruction caches, one or more data caches, and one or more translation lookaside buffers (TLBs). Instructions in the instruction caches may be copies of instructions in memory 530 or storage device 540. In some examples, the processor 520 may be configured (e.g., include programming stored thereon or executed thereby) to carry out one or more portions of any of the example methods or systems disclosed herein.

In some examples, the processor 520 is configured to perform any of the acts disclosed herein such as the act 430 in the method 400 or cause one or more portions of the computing device 510 or controller 500 to perform at least one of the acts disclosed herein. Such configuration can include one or more operational programs (e.g., computer program products) that are executable by the at least one processor 520. For example, the processor 520 may be configured to automatically transmit flow property at least related to a volume of the urine to the computing device 512. The computing device 512 may include the computing device 150 in urine collection systems 100, 200, 201, 300. The computing device 512 may include any aspect of the controller 500 described herein, such as one or more of a processor, a memory, a storage device, an I/O interface, and/or a communication interface. The computing device 512 can include one or more servers, one or more computers (e.g., desk-top computer, lap-top computer), or one or more mobile computing devices (e.g., smartphone, tablet, etc.).

The at least one computing device 510 (e.g., a server) may include at least one memory storage medium (e.g., memory 530 and/or storage device 540). The computing device 510 may include memory 530, which is operably coupled to the processor(s) 520. The memory 530 may be used for storing data, metadata, and programs for execution by the processor(s) 520. The memory 530 may include one or more of volatile and non-volatile memories, such as Random Access Memory (RAM), Read Only Memory (ROM), a solid state disk (SSD), Flash, Phase Change Memory (PCM), or other types of data storage. The memory 530 may be internal or distributed memory.

The computing device 510 may include the storage device 540 having storage for storing data or instructions. The storage device 540 may be operably coupled to the at least one processor 520. In some examples, the storage device 540 can comprise a non-transitory memory storage medium, such as any of those described above. The storage device 540 (e.g., non-transitory storage medium) may include a hard disk drive (HDD), a floppy disk drive, flash memory, an optical disc, a magneto-optical disc, magnetic tape, or a Universal Serial Bus (USB) drive or a combination of two or more of these. Storage device 540 may include removable or non-removable (or fixed) media. Storage device 540 may be internal or external to the computing device 510. In some examples, storage device 540 may include non-volatile, solid-state memory. In some examples, storage device 540 may include read-only memory (ROM). Where appropriate, this ROM may be mask programmed ROM, programmable ROM (PROM), erasable PROM (EPROM), electrically erasable PROM (EEPROM), electrically alterable ROM (EAROM), or flash memory or a combination of two or more of these. In some examples, one or more portions of the memory 530 and/or storage device 540 (e.g., memory storage medium(s)) may store one or more databases thereon. At least some of the databases may be used to store flow properties of the urine and/or flow volumes of the urine, as disclosed herein.

In some examples, flow properties of the urine may be stored in a memory storage medium such as one or more of the at least one processor 520 (e.g., internal cache of the processor), memory 530, or the storage device 540. In some examples, the at least one processor 520 may be configured to access (e.g., via bus 570) the memory storage medium(s) such as one or more of the memory 530 or the storage device 540. For example, the at least one processor 520 may receive and store the data (e.g., look-up tables) as a plurality of data points in the memory storage medium(s). The at least one processor 520 may execute programming stored therein adapted access the data in the memory storage medium(s) to automatically transmit a flow property at least related to a volume of the urine to the computing device 512. For example, the at least one processor 520 may access one or more flow property data tables in the memory storage medium(s) such as memory 530 or storage device 540.

The computing device 510 also includes one or more I/O devices/interfaces 550, which are provided to allow a user to provide input to, receive output from, and otherwise transfer data to and from the computing device 510. These I/O devices/interfaces 550 may include a mouse, keypad or a keyboard, a touch screen, camera, optical scanner, network interface, web-based access, modem, a port, other known I/O devices or a combination of such I/O devices/interfaces 550. The touch screen may be activated with a stylus or a finger.

The I/O devices/interfaces 550 may include one or more devices for presenting output to a user, including, but not limited to, a graphics engine, a display (e.g., a display screen or monitor), one or more output drivers (e.g., display drivers), one or more audio speakers, and one or more audio drivers. In certain examples, I/O devices/interfaces 550 are configured to provide graphical data to a display for presentation to a user. The graphical data may be representative of one or more graphical user interfaces and/or any other graphical content as may serve a particular implementation.

The computing device 510 can further include a communication interface 560. The communication interface 560 can include hardware, software, or both. The communication interface 560 can provide one or more interfaces for communication (such as, for example, packet-based communication) between the computing device 510 and one or more additional computing devices 512 or one or more networks. For example, communication interface 560 may include a network interface controller (NIC) or network adapter for communicating with an Ethernet or other wire-based network or a wireless NIC (WNIC) or wireless adapter for communicating with a wireless network, such as a WI-FI.

Any suitable network and any suitable communication interface 560 may be used. For example, computing device 510 may communicate with an ad hoc network, a personal area network (PAN), a local area network (LAN), a wide area network (WAN), a metropolitan area network (MAN), or one or more portions of the Internet or a combination of two or more of these. One or more portions of one or more of these networks may be wired or wireless. As an example, one or more portions of controller 500 or computing device 510 may communicate with a wireless PAN (WPAN) (such as, for example, a BLUETOOTH WPAN), a WI-FI network, a WI-MAX network, a cellular telephone network (such as, for example, a Global System for Mobile Communications (GSM) network), or other suitable wireless network or a combination thereof. Computing device 510 may include any suitable communication interface 560 for any of these networks, where appropriate.

The computing device 510 may include a bus 570. The bus 570 can include hardware, software, or both that couples components of computing device 510 to each other. For example, bus 570 may include an Accelerated Graphics Port (AGP) or other graphics bus, an Enhanced Industry Standard Architecture (EISA) bus, a front-side bus (FSB), a HYPER-TRANSPORT (HT) interconnect, an Industry Standard Architecture (ISA) bus, an INFINIBAND interconnect, a low-pin-count (LPC) bus, a memory bus, a Micro Channel Architecture (MCA) bus, a Peripheral Component Interconnect (PCI) bus, a PCI-Express (PCIe) bus, a serial advanced technology attachment (SATA) bus, a Video Electronics Standards Association local (VLB) bus, or another suitable bus or a combination thereof.

It should be appreciated that examples of acts described herein, such as the act 430 in the method 400 may be performed by and/or at the computing device 510

As used herein, the term "about" or "substantially" refers to an allowable variance of the term modified by "about" or "substantially" by ±10% or ±5%. Further, the terms "less than," "or less," "greater than," "more than," or "or more" include, as an endpoint, the value that is modified by the terms "less than," "or less," "greater than," "more than," or "or more."

While various aspects and embodiments have been disclosed herein, other aspects and embodiments are contemplated. The various aspects and embodiments disclosed herein are for purposes of illustration and are not intended to be limiting.

What is claimed is:
1. A urine collection system, comprising:
  a urine collection device configured to collect urine discharged from a user;
  a urine collection container in fluid communication with the urine collection device and sized and dimensioned to receive the urine discharged from the user;

a flow meter having a communication interface and positioned between the urine collection container and the urine collection device, wherein the flow meter is configured to detect a flow property of the urine at least related to a volume of the urine entering the urine collection container, and the communication interface is configured to wirelessly communicate to a computing device at least one of the detected flow property or the volume of the urine;

a first conduit in fluid communication with the urine collection device, wherein the flow meter is secured or securable to the first conduit and configured to detect the flow property of the urine passing through the first conduit before entering the urine collection container; and a pump configured to pull a vacuum and draw the urine from the urine collection device through the first conduit and into the urine collection container.

2. The urine collection system of claim 1, further comprising a second conduit in fluid communication with the urine collection container, wherein the flow meter is secured or securable to the second conduit between the first conduit and the second conduit and the pump is configured to pull the vacuum and draw the urine from the urine collection device through the first conduit, the flow meter, and the second conduit into the urine collection container.

3. The urine collection system of claim 2, further comprising a third conduit positioned between and in fluid communication with the urine collection container and the pump, wherein the urine collection container is a generally rigid urine collection container and the pump is configured to pull the vacuum through the third conduit effective to pull the vacuum and draw the urine from the urine collection device through the first conduit, the flow meter, and the second conduit into the generally rigid urine collection container.

4. The urine collection system of claim 3, wherein the generally rigid urine collection container is configured to be mounted to a bed frame.

5. The urine collection system of claim 1, wherein the urine collection container includes a urine collection bag.

6. The urine collection system of claim 5, further comprising:

a second conduit in fluid communication with the urine collection bag; and a pump secured or securable to the first conduit or the second conduit, wherein the pump is configured to pull a vacuum and draw the urine from the urine collection device through the first conduit and force the urine through the second conduit into the urine collection bag.

7. The urine collection system of claim 1, wherein the flow meter is configured to regulate the volume of the urine passing through the flow meter.

8. The urine collection system of claim 7, further comprising one or more valves associated with the first conduit configured to regulate the volume of urine passing through the first conduit, the one or more valves being configured to close and prevent the urine from passing through the first conduit when a predetermined volume of the urine has been collected in the urine collection container.

9. The urine collection system of claim 1, wherein the flow meter is position in-line with at least the first conduit.

10. The urine collection system of claim 1, wherein the flow meter is detachably secured or securable to the first conduit.

11. The urine collection system of claim 1, wherein:

the flow meter includes a display configured to display the volume of the urine entering the urine collection container during a selected period of time, the flow meter being configured to perform at least one of:
  detecting the flow property of the urine at least related to the volume of the urine entering the urine collection container with a mechanical detector;
  detecting the flow property of the urine at least related to the volume of the urine entering the urine collection container with an ultrasonic detector; or
  detecting at least one of a volume, a mass, or a velocity of the urine passing the flow meter; and the computing device is configured to perform at least one of:
  providing the volume of the urine entering the urine collection device in real-time using the at least one of the detected flow property or the volume of the urine communicated by the flow meter;
  transmitting the at least one of the detected flow property or the volume of the urine communicated by the flow meter to an electronic medical record system.

12. A method of determining a volume of urine discharged by a user, the method including:

receiving the urine discharged from the user in a urine collection device proximate to a urethra of the user;

detecting, with a flow meter, a flow property of the urine at least related to a volume of the urine discharged by the user as the urine is passed from the urine collection device to a urine collection container; and wirelessly transmitting, from a communication interface of the flow meter to a computing device, at least one of the detected flow property or the volume of the urine including the volume of the urine.

13. The method of claim 12, further comprising pulling a vacuum on a first conduit in fluid communication with the urine collection device effective to draw the urine from the urine collection device through the first conduit and into the urine collection container, wherein the flow meter is secured to the first conduit and configured to detect the flow property of the urine passing through the first conduit before entering the urine collection container.

14. The method of claim 13, wherein pulling a vacuum on a first conduit in fluid communication with the urine collection device includes pulling a vacuum on the first conduit in fluid communication with the urine collection device and a second conduit in fluid communication with the first conduit and the urine collection container effective to draw the urine from the urine collection device through the first conduit, the flow meter, and the second conduit into the urine collection container, wherein the flow meter is secured to the second conduit between the first conduit and the second conduit.

15. The method of claim 12, further comprising regulating the volume of the urine passing through the flow meter.

16. The method of claim 12, further comprising displaying, on a display on the flow meter, the volume of the urine entering the urine collection container during a selected period of time.

17. The method of claim 12, further comprising providing, with the computing device, the volume of the urine entering the urine collection device in real-time using the at least one of the detected flow property or the volume of the urine communicated by the flow meter.

18. The method of claim 12, further comprising transmitting, with the computing device, the at least one of the detected flow property or the volume of the urine communicated by the flow meter including the volume of the urine to an electronic medical record system.

19. The method of claim 12, wherein detecting, with a flow meter, a flow property of the urine at least related to a volume of the urine discharged by the user includes detecting, with the flow meter, at least one of a volume, a mass, or a velocity of the urine passing the flow meter.

20. A urine collection system, comprising:
- a urine collection device configured to collect urine discharged from a user;
- a urine collection container in fluid communication with the urine collection device and sized and dimensioned to receive the urine discharged from the user;
- a flow meter having a communication interface and positioned between the urine collection container and the urine collection device, wherein the flow meter is configured to detect a flow property of the urine at least related to a volume of the urine entering the urine collection container, and the communication interface is configured to wirelessly communicate to a computing device at least one of the detected flow property or the volume of the urine;

wherein:
the urine collection device includes a funnel-shaped urine collection device seat having a wide end and a narrow end, the funnel-shaped urine collection seat sized and dimensioned for the user to sit on the funnel-shaped urine collection seat; and
the flow meter is secured or securable to the narrow end of the funnel-shaped urine collection device.

21. The urine collection system of claim 20, wherein the urine collection container is positioned below the funnel-shaped urine collection seat, and is sized and dimensioned to support the funnel-shaped urine collection seat.

22. A method of determining a volume of urine discharged by a user, the method including:
- receiving the urine discharged from the user in a urine collection device in a funnel-shaped urine collection seat having a wide end and a narrow end;
- detecting, with the flow meter secured to the narrow end of the funnel-shaped urine collection seat, the flow property of the urine at least related to the volume of the urine discharged by the user as the urine is passed from the funnel-shaped urine collection seat to the urine collection container; and
- wirelessly transmitting, from a communication interface of the flow meter to a computing device, at least one of the detected flow property or the volume of the urine including the volume of the urine.

23. The method of claim 16, further comprising positioning the funnel-shaped urine collection seat on the urine collection container.

* * * * *